US011849933B2

(12) United States Patent
Denham et al.

(10) Patent No.: US 11,849,933 B2
(45) Date of Patent: Dec. 26, 2023

(54) BONE ALIGN AND JOINT PREPARATION DEVICE AND METHOD

(71) Applicant: Nextremity Solutions, Inc., Warsaw, IN (US)

(72) Inventors: Greg Denham, Warsaw, IN (US); Ryan Schlotterback, Fort Wayne, IN (US); Daren Granger, Warsaw, IN (US)

(73) Assignee: MEDARTIS AG, Basel (CH)

( * ) Notice: Subject to any disclaimer, the term of this patent is extended or adjusted under 35 U.S.C. 154(b) by 253 days.

(21) Appl. No.: 17/238,920

(22) Filed: Apr. 23, 2021

(65) Prior Publication Data

US 2021/0330311 A1    Oct. 28, 2021

Related U.S. Application Data

(60) Provisional application No. 63/015,052, filed on Apr. 24, 2020.

(51) Int. Cl.
*A61B 17/02* (2006.01)
*A61B 17/15* (2006.01)
(Continued)

(52) U.S. Cl.
CPC ............ *A61B 17/025* (2013.01); *A61B 17/15* (2013.01); *A61B 17/151* (2013.01);
(Continued)

(58) Field of Classification Search
CPC ..... A61B 17/025; A61B 17/15; A61B 17/151; A61B 17/1775; A61B 2017/564; A61B 2017/565; A61B 2017/681; A61B 17/66
See application file for complete search history.

(56) References Cited

U.S. PATENT DOCUMENTS 8,235,994 B2 *   8/2012   Hollawell .......... A61B 17/6475
                                                              606/59
2016/0235414 A1   8/2016   Hatch et al.
(Continued)

FOREIGN PATENT DOCUMENTS

| EP | 1508316 A1 | 2/2005 |
| GB | 2583572 A | 11/2020 |
| GB | 2589960 A | 6/2021 |

OTHER PUBLICATIONS

UKIPO Search Report dated Sep. 20, 2021.
UKIPO Search Report dated Feb. 23, 2021.

*Primary Examiner* — Larry E Waggle, Jr.
(74) *Attorney, Agent, or Firm* — Heslin Rothenberg Farley & Mesiti P.C.; Victor A Cardona, Esq.

(57) ABSTRACT

A bone displacement system includes an anchoring portion, a tool engaging portion, a compression distraction mechanism, a lateral body and a distal body. The anchoring portion has an aperture for receiving a wire to connect the anchoring portion to a proximal bone. The tool engaging portion is connected to the anchoring portion and is configured to connect a tool thereto. The compression-distraction mechanism is connected to the anchoring portion. The lateral body is connected to the compression-distraction mechanism by a ratchet. The lateral body has a downwardly depending portion for contacting a lateral bone. The distal body is connected to the compression-distraction mechanism. The distal body has an aperture for receiving a wire to connect the distal body to a distal bone. The compression-distraction mechanism is configured to move the anchoring portion relative to the distal body.

24 Claims, 23 Drawing Sheets

(51) Int. Cl.
  *A61B 17/56*  (2006.01)
  *A61B 17/68*  (2006.01)
  *A61B 17/17*  (2006.01)

(52) U.S. Cl.
  CPC .... *A61B 17/1775* (2016.11); *A61B 2017/564* (2013.01); *A61B 2017/565* (2013.01); *A61B 2017/681* (2013.01)

(56) References Cited

U.S. PATENT DOCUMENTS

| | | |
|---|---|---|
| 2017/0014143 A1* | 1/2017 | Dayton .............. A61B 17/8061 |
| 2017/0020537 A1 | 1/2017 | Tuten |
| 2017/0079669 A1 | 3/2017 | Bays et al. |
| 2019/0274745 A1 | 9/2019 | Smith et al. |
| 2021/0077131 A1 | 3/2021 | Denham et al. |

* cited by examiner

BONE ALIGN AND JOINT PREPARATION DEVICE AND METHOD

CROSS-REFERENCE TO RELATED APPLICATIONS

The present application claims priority to U.S. Provisional Application Ser. No. 62/015,052 filed on Apr. 24, 2020, which is incorporated herein by reference in its entirety.

The present application is related to U.S. application Ser. No. 17/022,761 filed Sep. 16, 2020, which claims the benefit of U.S. Provisional Application Ser. No. 62/900,920 filed Sep. 16, 2019, U.S. Provisional Application No. 62/991,879 filed Mar. 19, 2020, and U.S. Provisional Application No. 63/015,052 filed Apr. 24, 2020, which are incorporated herein by reference in their entireties.

FIELD OF THE INVENTION

This application relates to apparatuses, devices, and methods for adjusting and joining bones.

DESCRIPTION OF THE RELATED ART

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The bunion is a disease of the joint and soft tissue. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and, in some cases, very painful during walking and other weight bearing activities. Bunions may also be painful and debilitating condition that prevents wearing shoes. Genetics and poor shoe design are the causes. The angle between the metatarsal of the second digit is a means to quantify the degree of deformity.

Painful bunions are corrected by surgical soft tissue management and surgical bone reforming. The first metatarsal is corrected by sectioning it with a saw and moving the head laterally. There are numerous cut locations from the proximal to distal regions, namely the chevron, Ludloff, Mau and proximal. The bones are shifted, and held in place with screws, staples or plates. Sometimes adjacent joints are fused to stabilize the reconstruction.

The Lapidus procedure is a type of fusion of the first TMT joint that decreases the movement of that joint and straightens out the first metatarsal and toe, so the Lapidus procedure treats bunions caused by first TMT joint hypermobility.

The goal of the Lapidus procedure is to surgically treat hallux valgus that is caused by first TMT joint hypermobility. An orthopedic foot and ankle surgeon realigns to a normal toe shape by placing the first metatarsal straight with the medial cuneiform bone and locking or fusing these two bones together. When the first TMT joint is fused, the first metatarsal will not move abnormally. This will allow the first toe to stay straight and prevent the bunion from coming back.

Thus, a need exists for devices, systems, and methods for treating foot deformities that are repeatable yet adaptable to particular clinical situations.

SUMMARY OF THE INVENTION

The present invention provides, in a first aspect, a bone displacement system which includes an anchoring portion, a tool engaging portion, a compression distraction mechanism, a lateral body and a distal body. The anchoring portion has an aperture for receiving a wire to connect the anchoring portion to a proximal bone. The tool engaging portion is connected to the anchoring portion and is configured to connect a tool thereto. The compression-distraction mechanism is connected to the anchoring portion. The lateral body is connected to the compression-distraction mechanism by a ratchet. The lateral body has a downwardly depending portion for contacting a lateral bone. The distal body is connected to the compression-distraction mechanism. The distal body has an aperture for receiving a wire to connect the distal body to a distal bone. The compression-distraction mechanism is configured to move the anchoring portion relative to the distal body.

The present invention provides, in a second aspect, a method for use in bone displacement which includes inserting a first wire through an anchoring portion of a bone displacement mechanism into a first bone. An alignment paddle is releasably connected to the bone displacement mechanism. The paddle is inserted between a first bone and a second bone. A second wire is inserted through a distal body of the bone displacement mechanism distal to the anchoring portion into a second bone distal to the first bone. The distal body and the second bone are moved toward a lateral body of the bone displacement mechanism located laterally relative to the distal body and the anchoring portion to adjust an alignment of axes of the first bone and the second bone relative to each other.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DETAILED DESCRIPTION OF THE EMBODIMENTS

Figure 1:
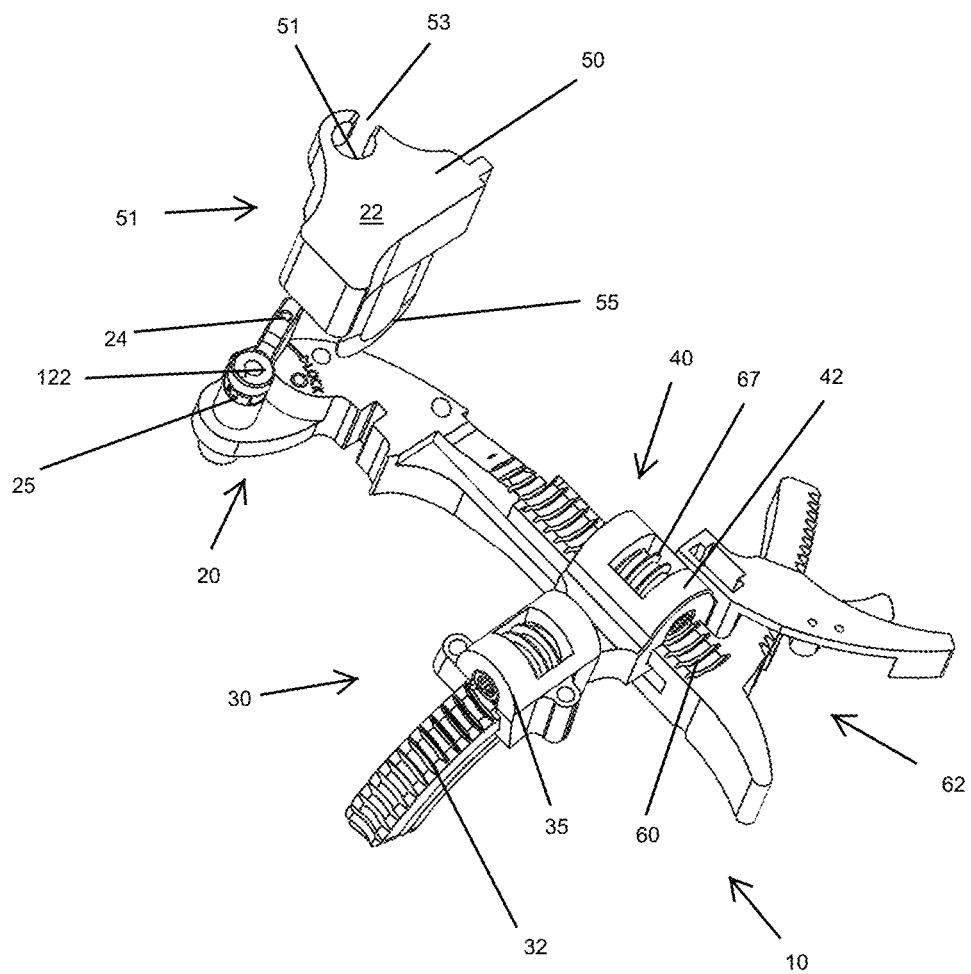
FIG. 1 is a perspective view of a cut guide system having a paddle cartridge shown separated therefrom.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As will be described below, the present invention includes systems and methods for correcting a deformity of the human foot. As depicted in FIGS. 1-31, a cut guide and bone displacement system 10 may include a cartridge engaging portion 20, a distal body, such as a pronation alignment trolley 30, and an intermediate body, such as a compression-distraction mechanism 40. Cartridge engaging portion 20 may have an upwardly projecting portion 25 configured to engage a receiving portion of a tool, such as a paddle cartridge 50, for example.

Alignment trolley 30 may include a mobile or holding portion 35 holding a worm screw 31 received within a recess 37 and movably engaged with teeth 33 to move along an axis of a threaded rail 32.

A connecting portion 45 may connect trolley 30 with compression-distraction mechanism 40. Compression-distraction mechanism 40 may include a mobile portion 42 engageable with an arm 60 connected to cartridge engaging portion 20. Mobile portion 42 may be movable along a longitudinal axis of arm 60. A worm screw 67 may move mobile portion 42 relative to arm 60, as described below, thereby moving alignment trolley 30 relative to arm 60. Arm 60 and rail 32 may have axes aligned perpendicular to each other, or approximately or about perpendicular.

Figure 2:
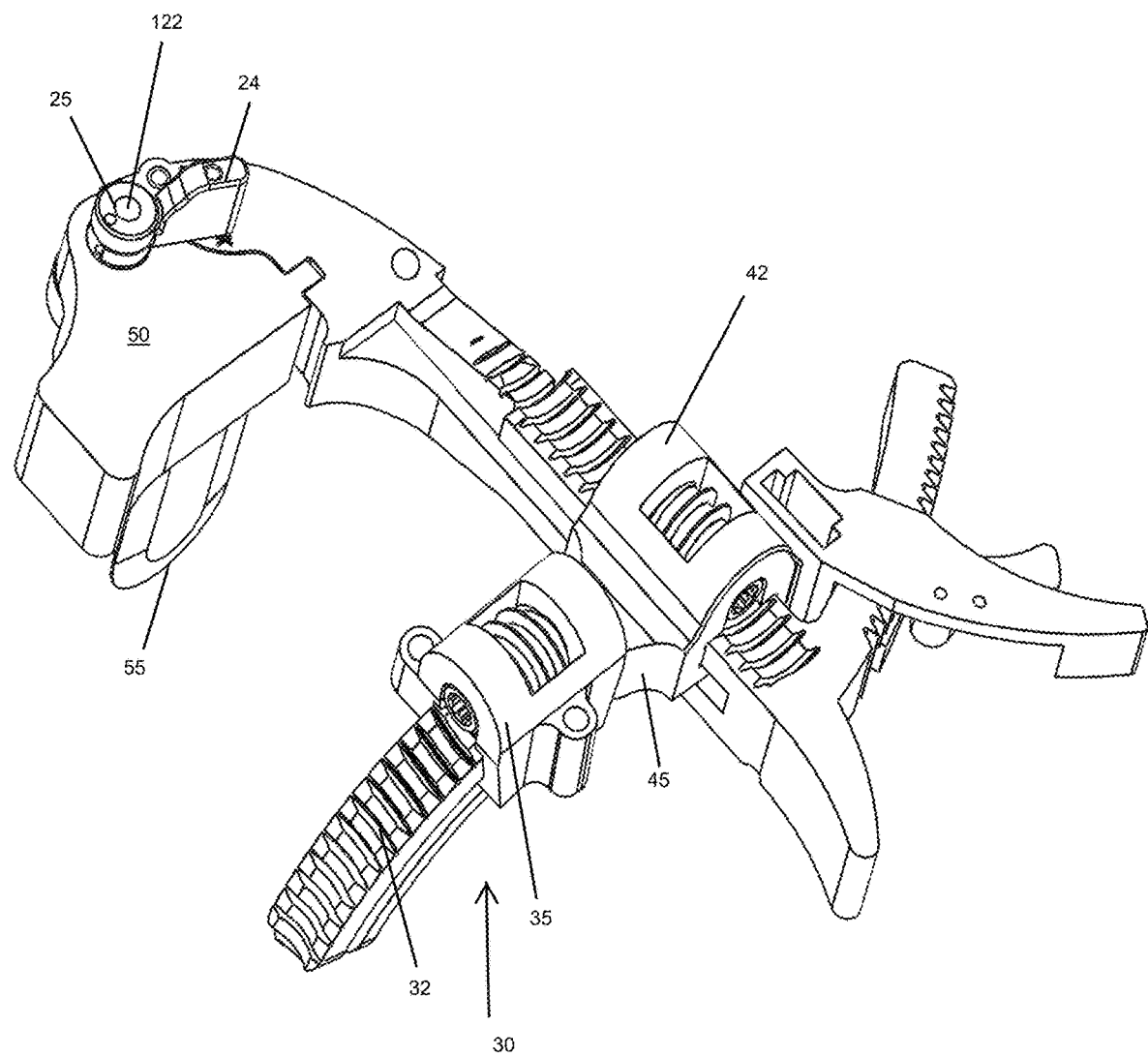
FIG. 2 is a perspective view of the system of FIG. 1 with the paddle cartridge connected to a cartridge engaging portion of the system.
Figure 3:
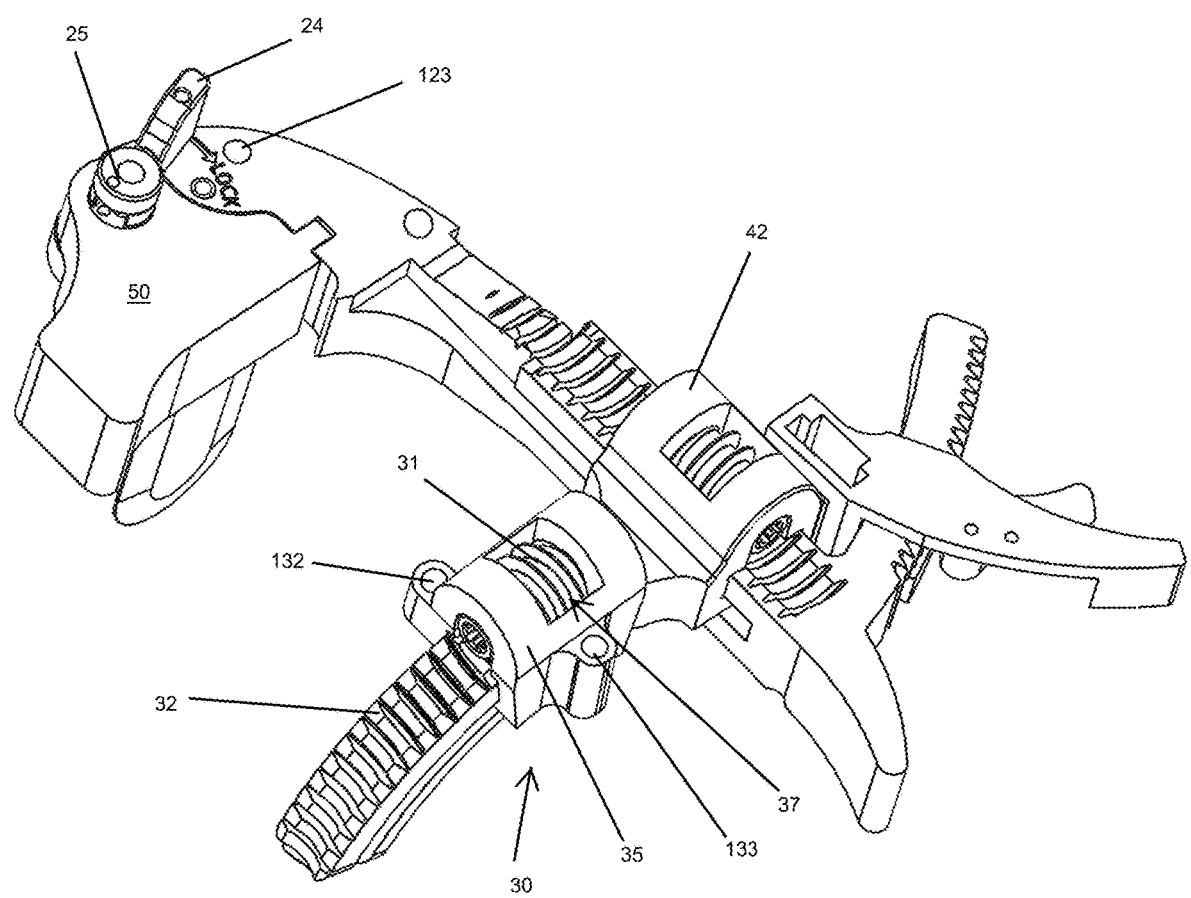
FIG. 3 is a top view of the cartridge engaging portion of the system of FIG. 1 with the paddle cartridge engaged thereto in an unlocked condition.

As depicted in FIGS. 1-2, a paddle cartridge 50 may include a receiving opening 51 and a slot 53 to receive a pin or upwardly projecting portion 25 and a handle 24, respectively, to releasably connect paddle cartridge 50 to cartridge engaging portion 20. Upwardly projecting portion 25 and handle 24 may be inserted through opening 51 and slot 53 such that handle 24 is above a top surface 22 of cartridge 50 and may be rotated such that handle 24 is located above and/or contacting top surface 22 to fix a cartridge (e.g., cartridge 50) into a connection with cartridge engaging portion 20 In particular, receiving opening 51 may be cylindrical for receiving upwardly projecting portion 25 which may also be cylindrical to allow a rotation of upwardly projecting portion 25 within receiving opening 51 to secure paddle cartridge 50 to cartridge engaging portion 20 as handle 24 is located above top surface 22 as depicted in FIG. 2 in a locked position. FIG. 3 depicts hands 24 after being inserted through receiving opening 51 but prior to such rotation.

Figure 4:
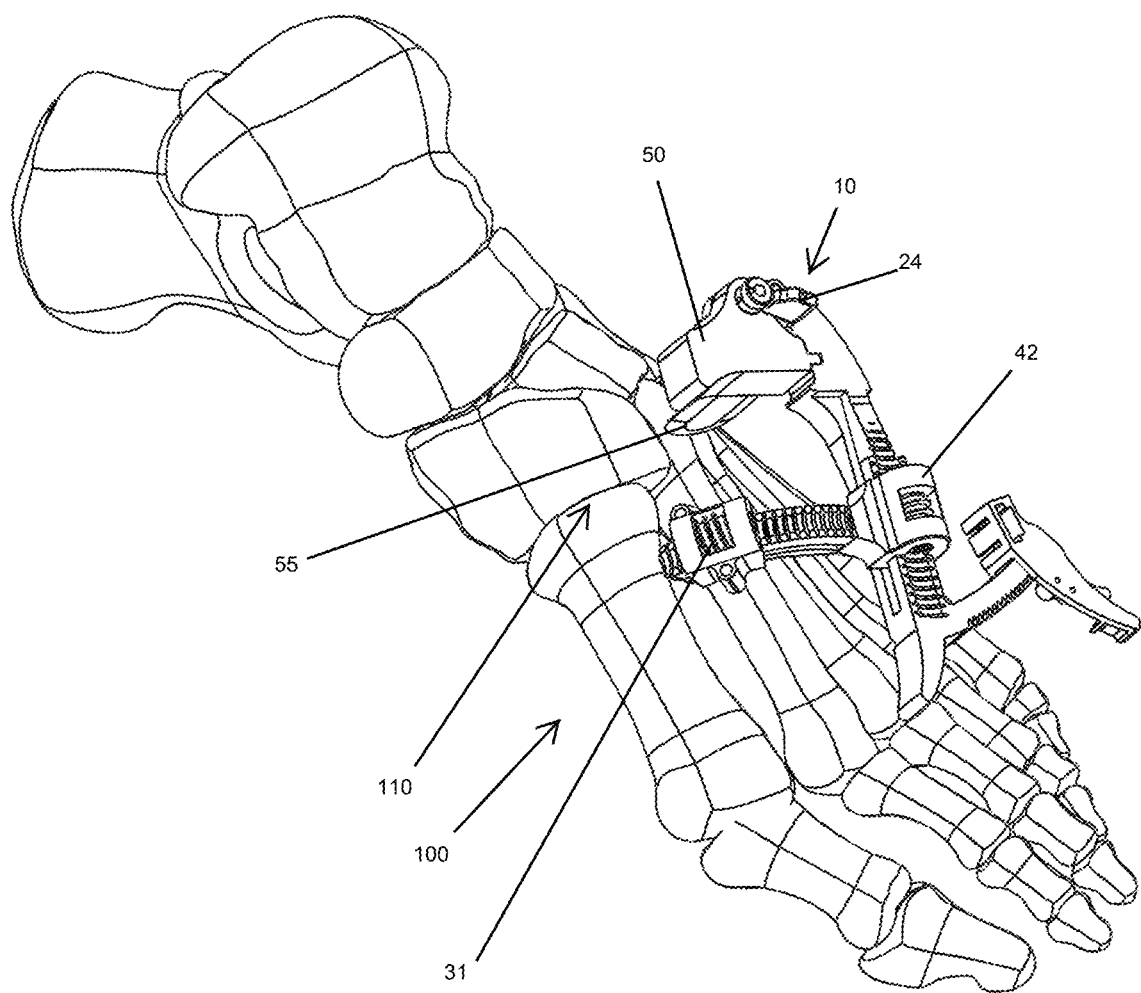
FIG. 4 is a top view of the cartridge engaging portion of the system of FIG. 1 with the paddle cartridge locked to the cartridge engaging portion.
Figure 5:
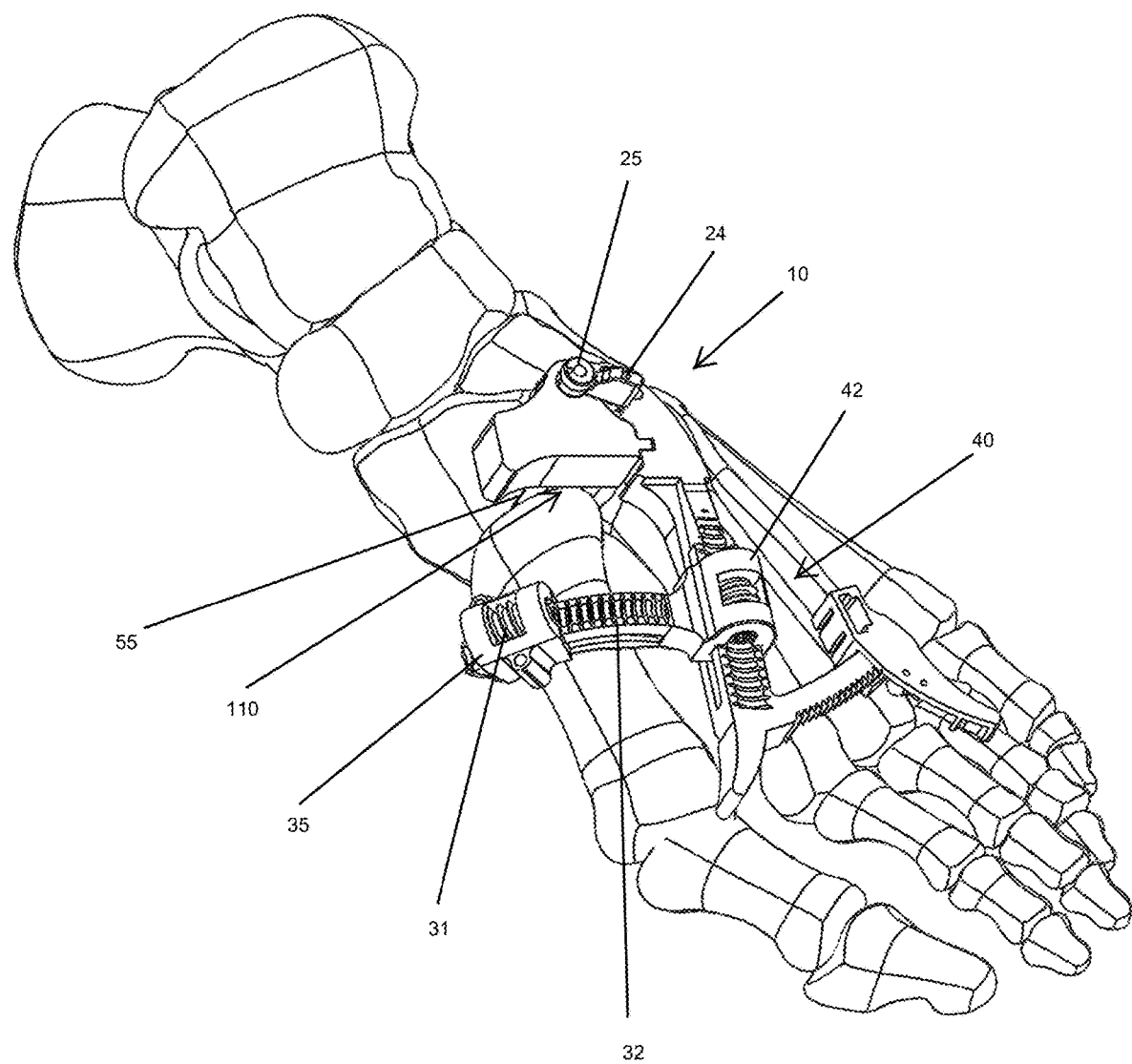
FIG. 5 is a perspective view of the system of FIG. 1 engaged with a foot with a paddle of the paddle cartridge received in a joint between a cuneiform and a metatarsal of the foot.
Figure 6:
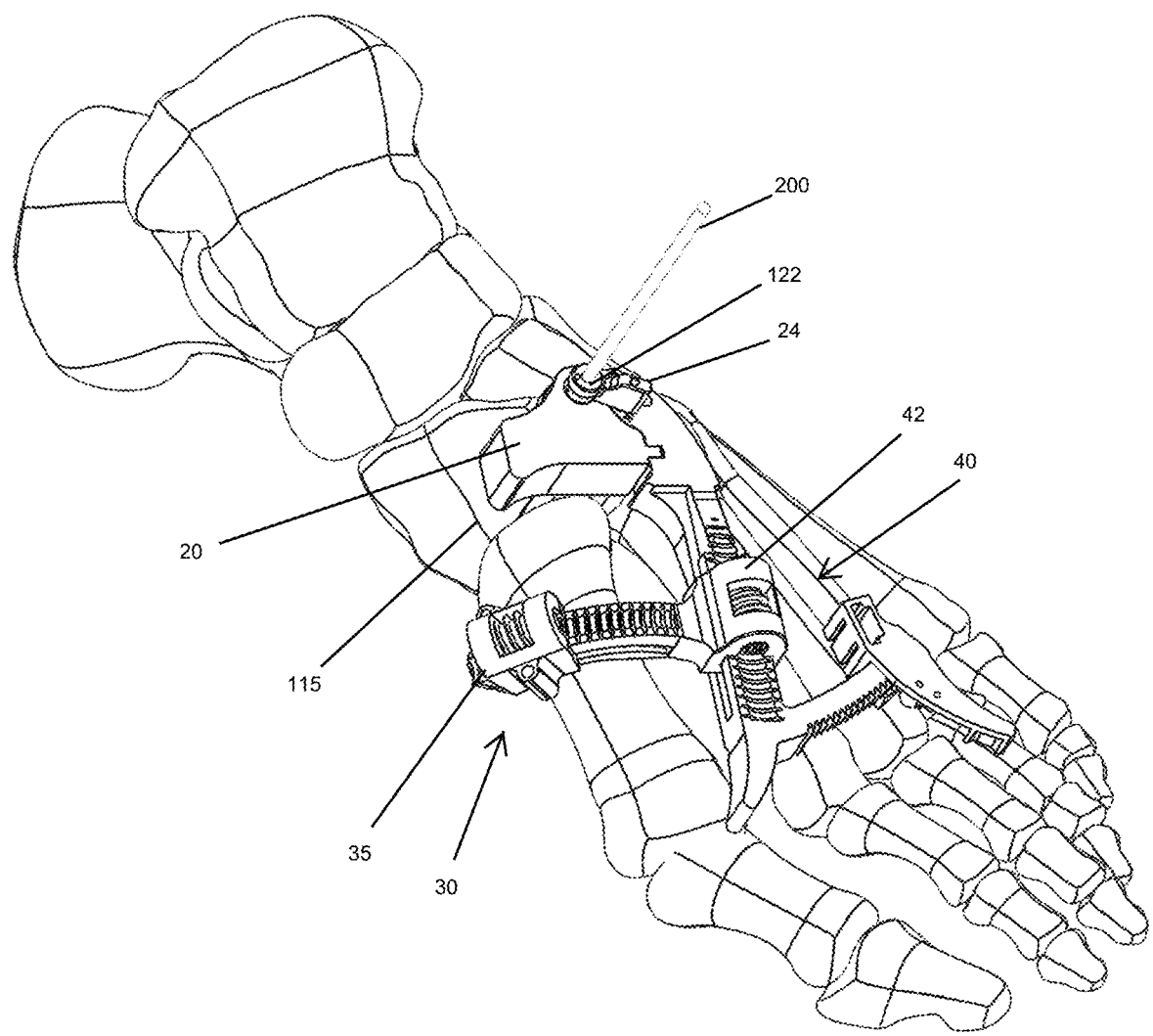
FIG. 6 is a perspective view of the system of FIG. 5 with a K-wire connecting the cartridge engaging portion with the cuneiform.

As depicted in FIGS. 4-6, system 10 may be engaged with a foot 100 by a downwardly depending joint arm or paddle 55 of paddle cartridge 50 being received in a first tarsometatarsal joint space 110 to align system 10 relative to foot 100. A threaded pin or K-wire 200 may be inserted through a hole 122 in upwardly projecting portion 25 of cartridge engaging portion 20 received in receiving opening 51 into a proximal cuneiform 115 of foot 100 as depicted in FIG. 6.

A second k-wire 210 may be inserted through a second opening 132 of holding portion 35 of trolley 30 and a third k-wire 211 may be inserted through a third opening 133 of holding portion 35 of trolley 30 to fix trolley 30 relative to a first metatarsal 117 as depicted in FIG. Second opening 132 and third opening 133 may have axes which are diverging such that top ends of second k-wire 210 and third k-wire 211 may be closer to one another than bottom ends thereof when the k-wires extend through second opening 132 and third opening 133 and into first metatarsal 117.

Figure 7:
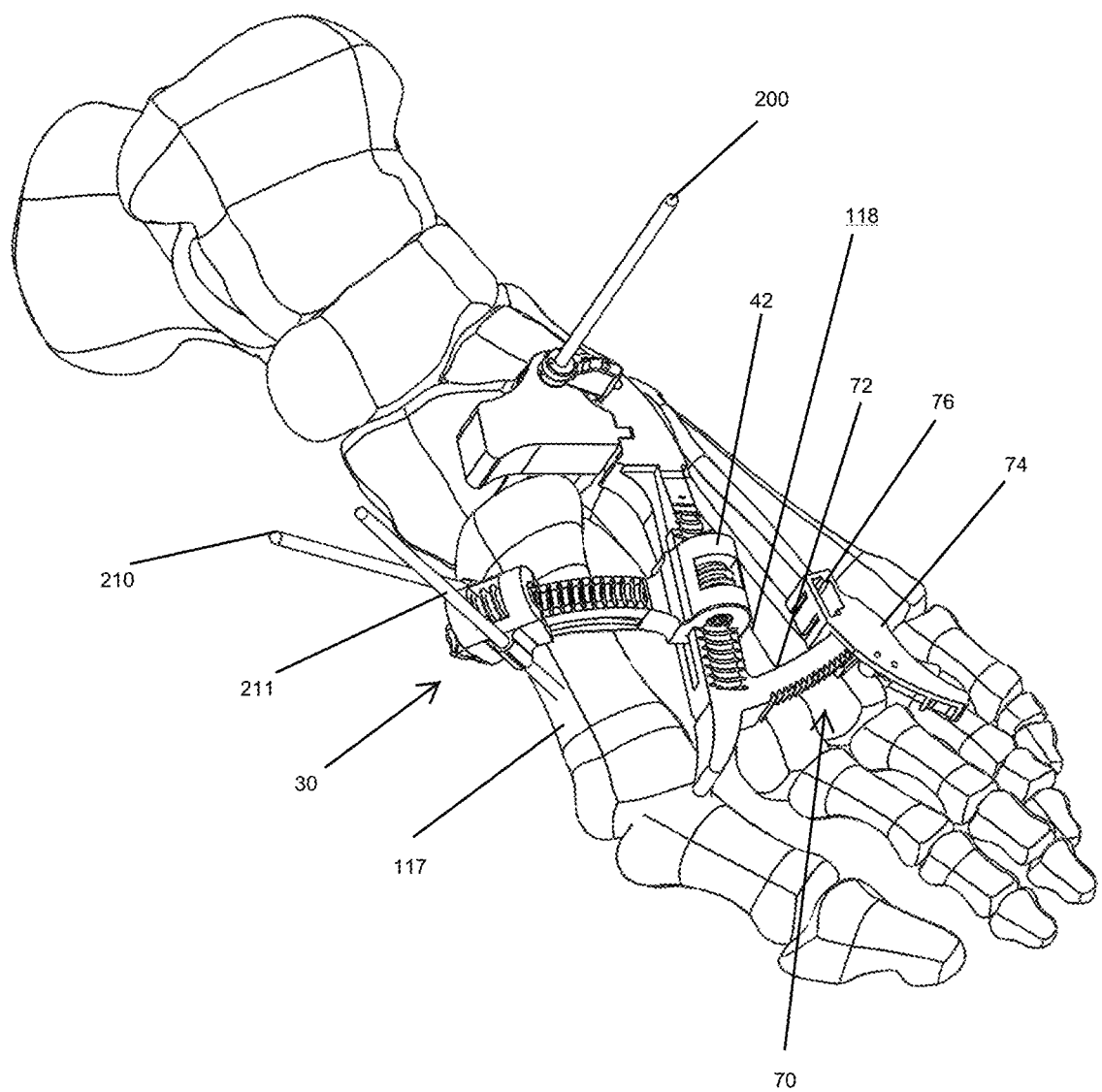
FIG. 7 a top view of the cartridge engaging portion of the system of FIG. 6 showing the paddle cartridge locked to the cartridge engaging portion and a K-wire connecting a holding portion of a trolley with the metatarsal.
Figure 8:
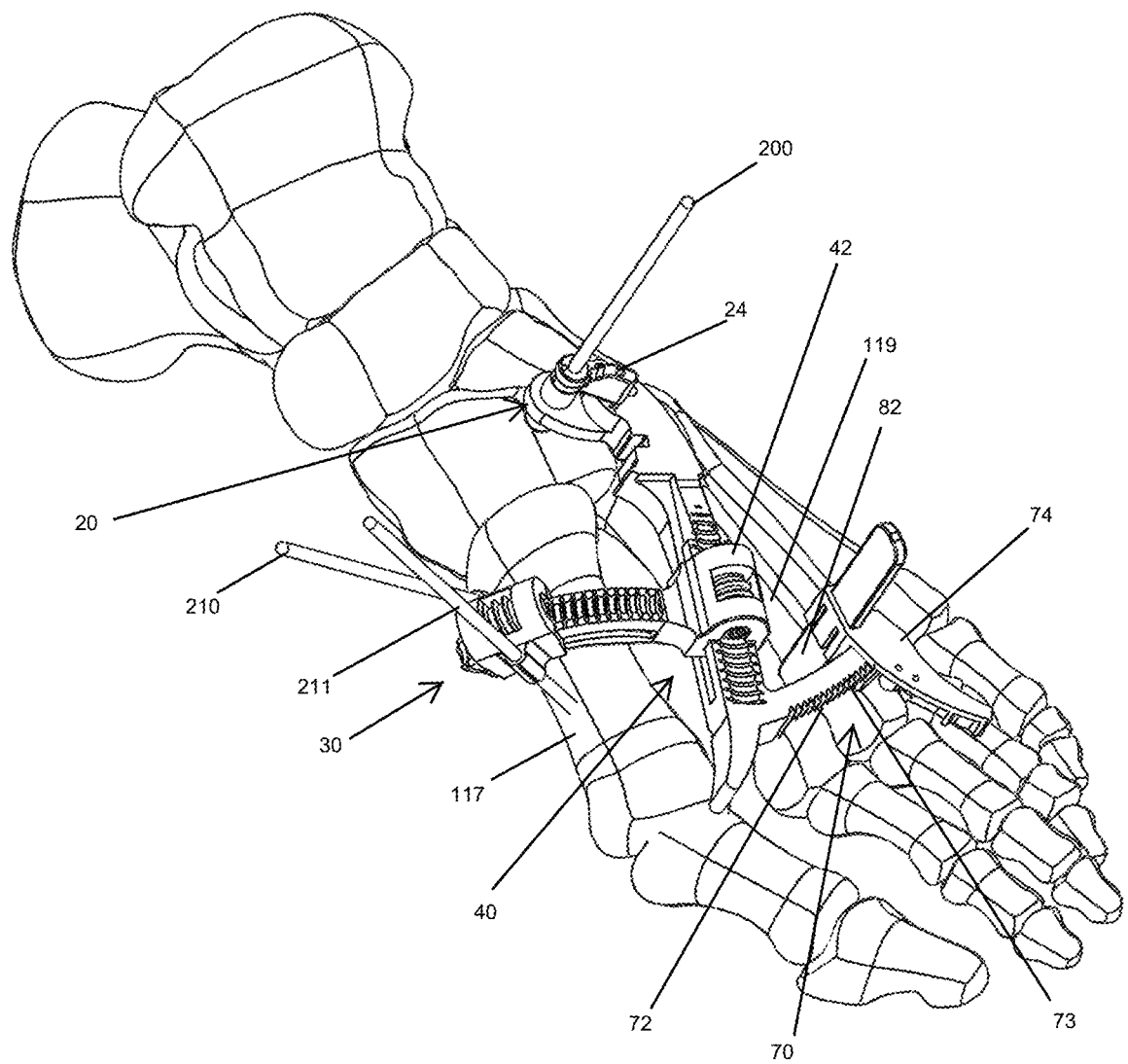
FIG. 8 is a perspective view of the system of FIG. 7 with the paddle cartridge removed and a paddle received in a lateral body.

As depicted in FIG. 8 relative to FIG. 7, paddle cartridge 50 may then be removed from K-wire 200 after handle 24 and upwardly projecting portion 25 are rotated (e.g., counterclockwise) to allow handle 24 and upwardly projecting portion 25 to pass upwardly through receiving opening 51 and slot 53.

A ratcheting mechanism 70 may be connected to distraction mechanism 40 by a ratchet arm 72 connected to a ratchet body 74. A paddle 82 may be received in a receiving cavity 76 of ratchet body 74 such that paddle 82 may extend through cavity 76 and may abut a side of a third metatarsal 119 adjacent a second metatarsal 118, as depicted in FIG. 8.

Figure 9:
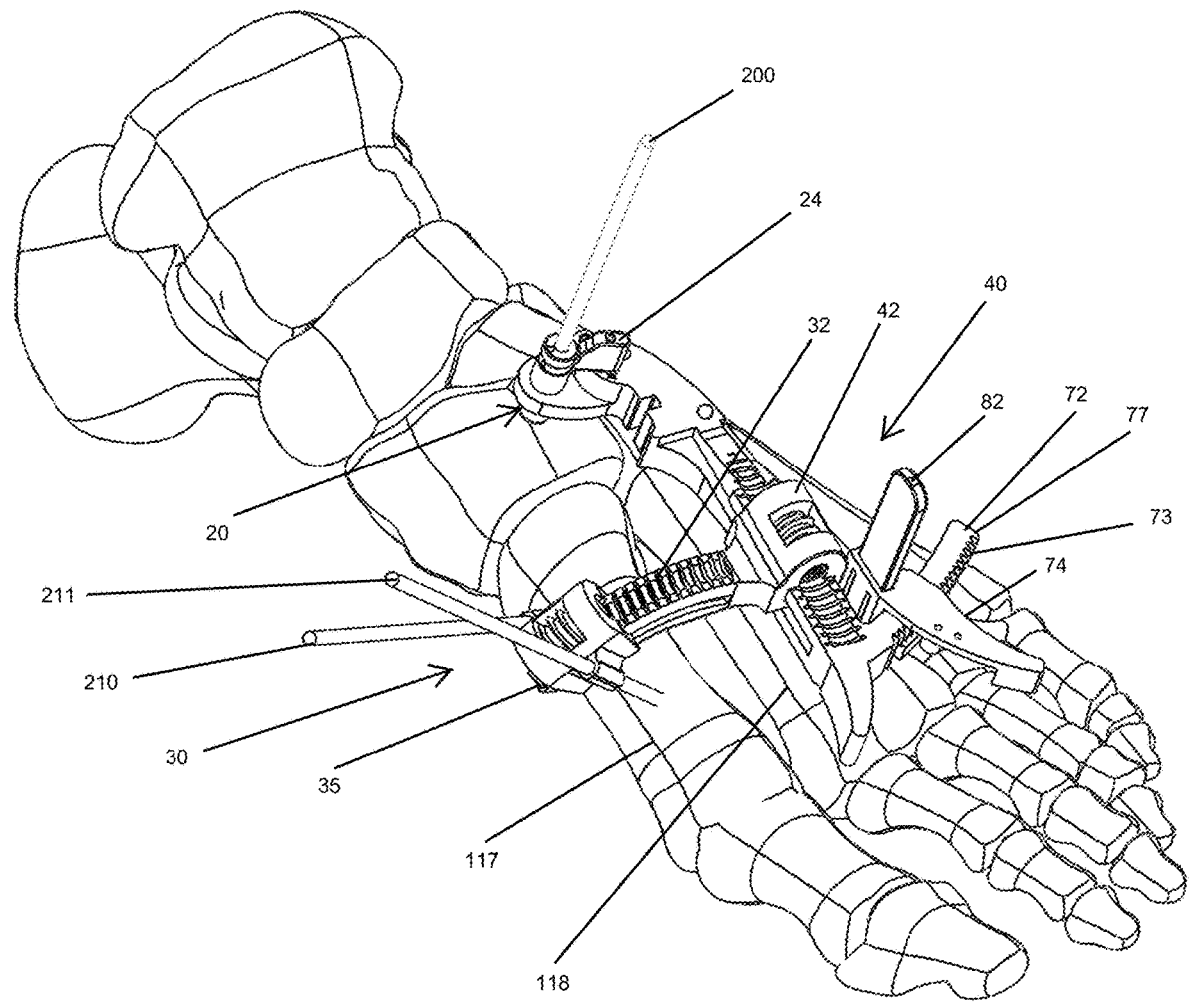
FIG. 9 is a perspective view of the system of FIG. 8 with a compression-distraction mechanism moved on a ratchet toward the lateral body and axes of the metatarsal and a second metatarsal aligned.

A valgus angle of first metatarsal 117 may be reduced by hand (e.g., by a surgeon) as shown comparing FIG. 8 to FIG. 9. Such movement of first metatarsal 117 may cause ratchet body 74 to move along ratchet arm 72 (i.e., due to a resistance provided by paddle 82 against third metatarsal 119) such that teeth 73 of arm 72 may contact a pawl (not shown) of body 74 and such that ratchet arm 72 may extend under ratchet body with an end 77 of ratchet arm 72 extending away from holding portion 35 and such that compression-distraction mechanism 40 moves over second metatarsal 118 third metatarsal, for example. The movement of ratchet arm 72 away from holding portion 35 and engagement of teeth 73 with the ratchet may be a releasable ratcheting such that a movement in an opposite direction (e.g., away from a lateral body (i.e., ratchet body 74)) may be inhibited by a contact of the ratchet with teeth 73. Upon release of the pawl from one of teeth 73, ratchet arm 72 may move freely away from the pawl (e.g., toward trolley 30).

Figure 10:
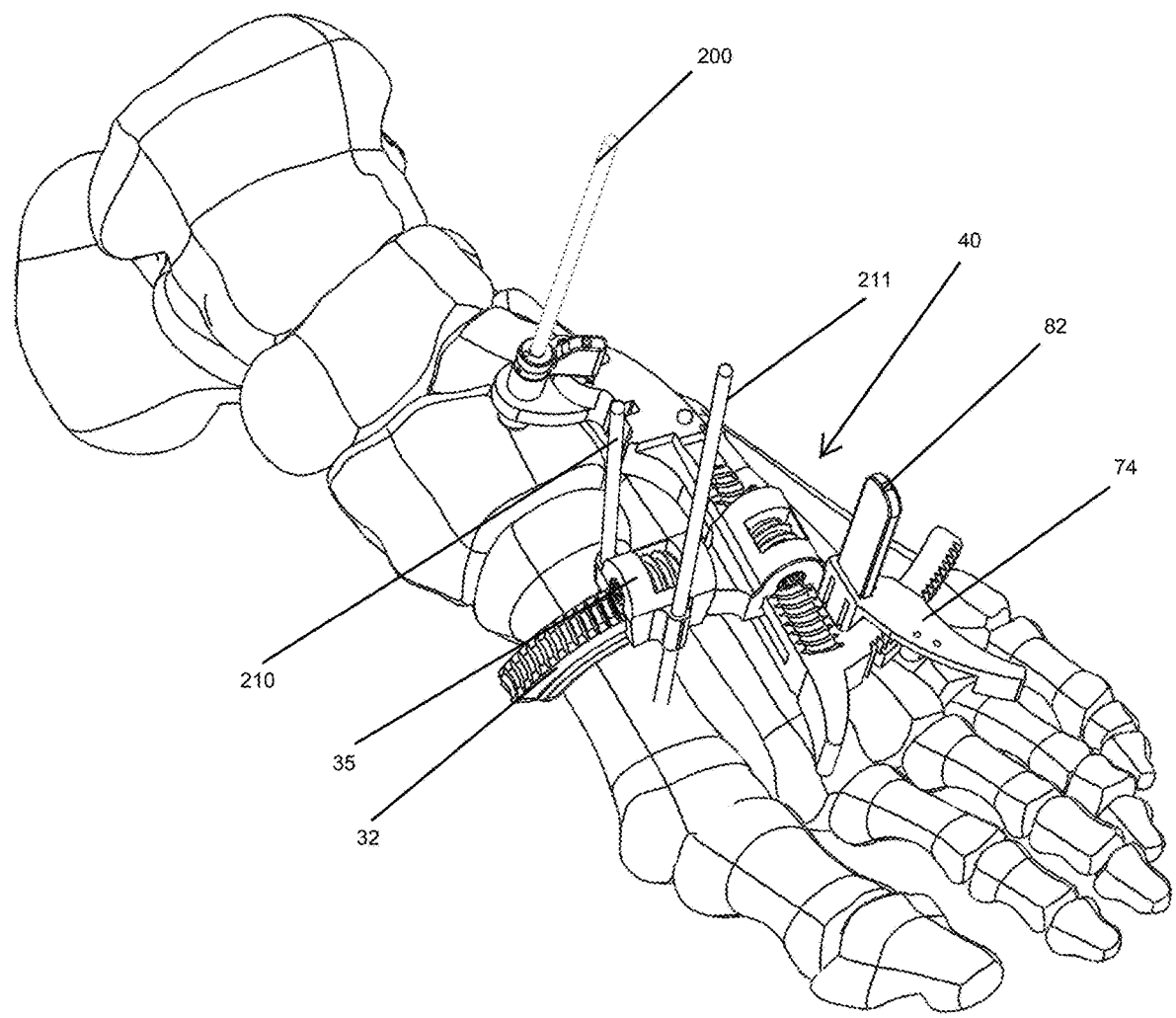
FIG. 10 is a perspective view of the system of FIG. 11 with a trolley holding portion rotated to correct a valgus angle of the first metatarsal.
Figure 11:
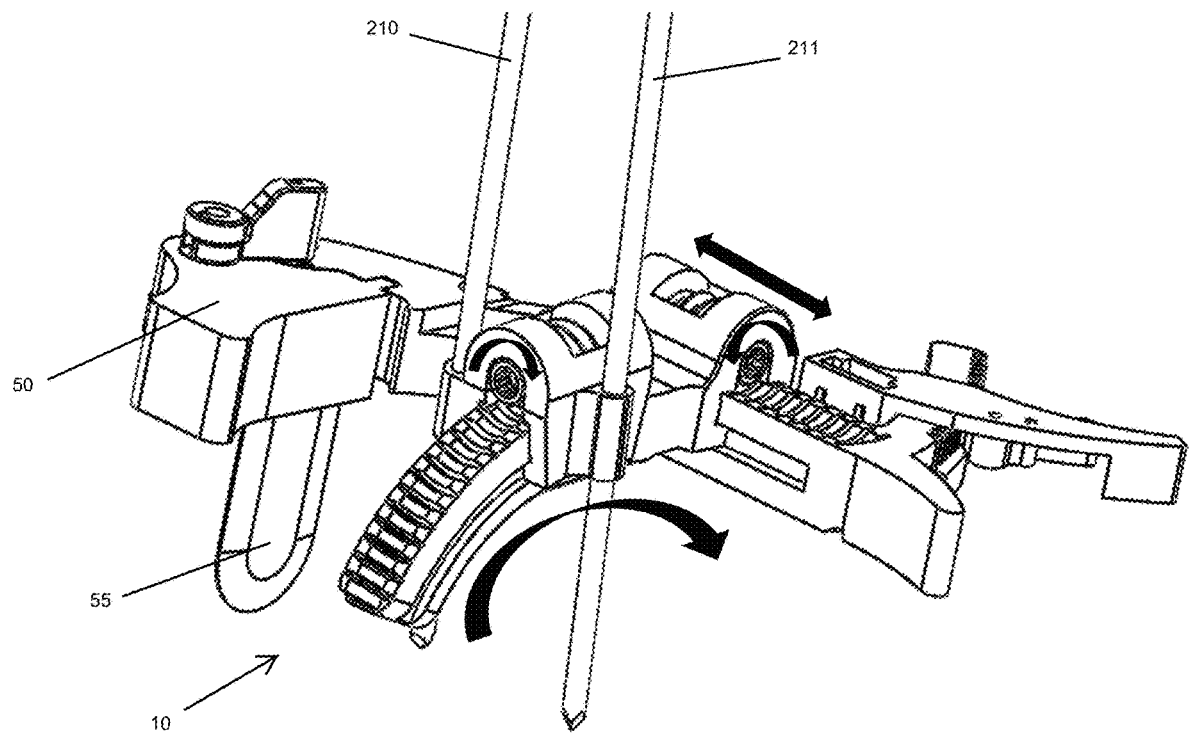
FIG. 11 is perspective view of the trolley of FIG. 9 with a mobile portion moved on rails thereof.
Figure 12:
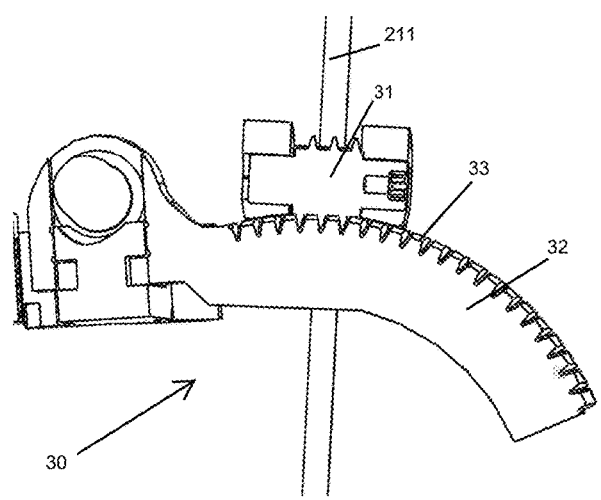
FIG. 12 is a side cross-sectional view of the trolley of FIG. 10.

As depicted in FIGS. 10-12, holding portion 35 may be moved (e.g., via a manipulation or rotation of worm screw 31 by a user) along rail 32 of trolley 30 until a longitudinal dimension of k-wire 210 is perpendicular or about perpendicular to longitudinal dimensions of sesamoids (not shown) of first metatarsal 117. Such movement of holding portion 35 connected to first metatarsal 117 by second k-wire 210 and third k-wire 211 may further adjust the valgus angle of first metatarsal 117.

FIG. 11 shows system 10 separate from foot 100 with paddle 55, but not paddle 82, and after worm gear 31 has driven trolley 30 along rail 32 as described above with holding portion 35 at a top of an arc of rail 32. FIG. 12 depicts a side cross sectional view of FIG. 11 along an axis of rail 32 looking away from paddle with second wire 210 and third wire 211 aligned in a perpendicular direction relative to a longitudinal dimension of rail 32.

Figure 13:
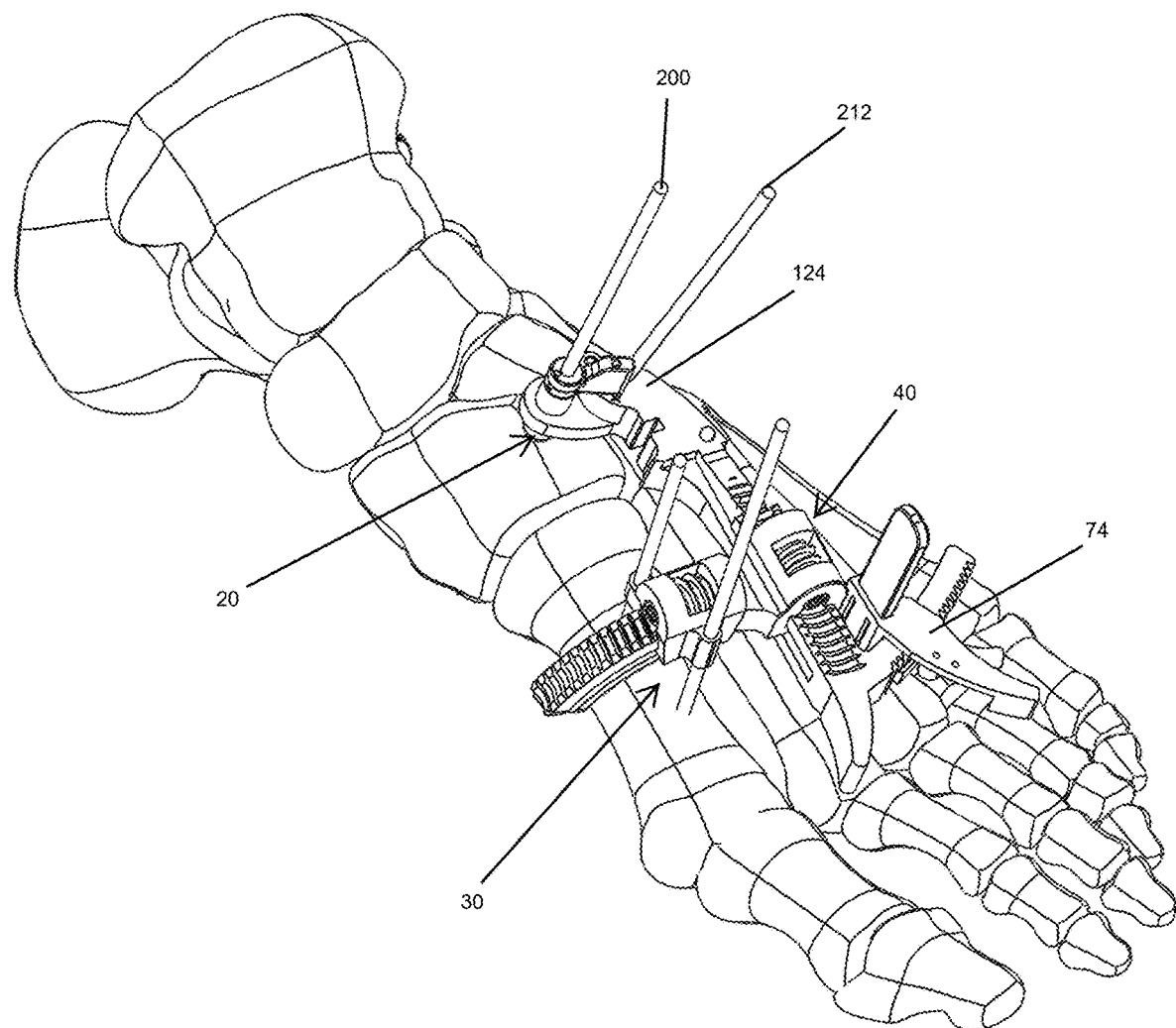
FIG. 13 depicts a perspective view of the system of FIG. 10 with a K-wire connecting an anchoring portion with the foot.

As depicted in FIG. 13, a fourth k-wire 212 may be inserted through an anchoring hole 123 (FIG. 3) in an anchoring or connecting portion 124 between cartridge engaging portion 20 and distraction mechanism 40 to hold system 10 relative to foot 100 after holding portion 35 is moved on rails 32 and first metatarsal 117 is thus rotated.

Figure 14:
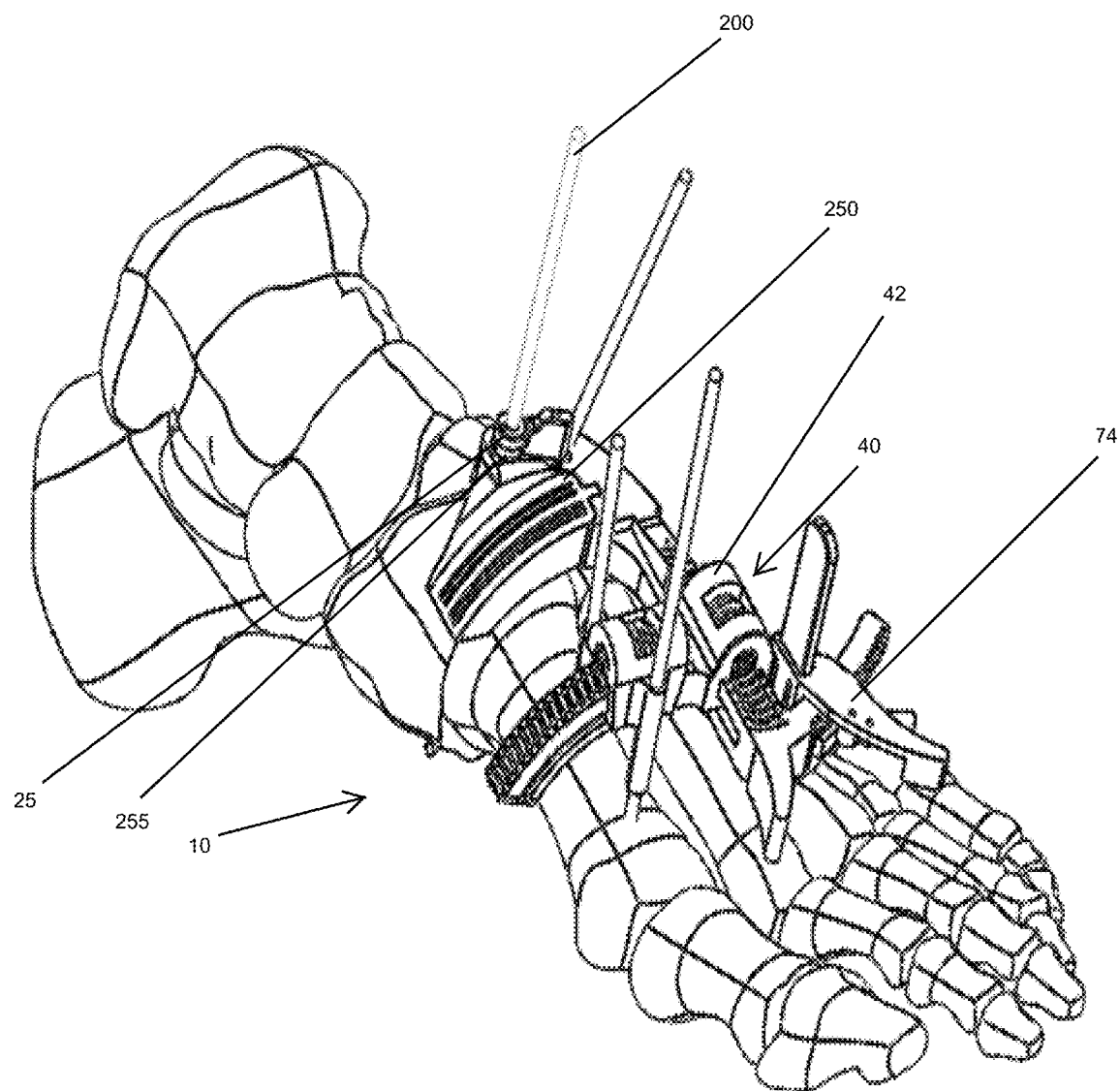
FIG. 14 depicts a perspective view of the system of FIG. 13 with an open cut guide connected to the cartridge engaging portion.

As depicted in FIG. 14, an open saw guide 250 may be attached to cartridge engaging portion 20 in a same manner as described above for attaching paddle cartridge 50 to cartridge engaging portion 20. Open saw guide 250 may have a recess 255 for receiving upwardly projecting portion 25 and handle 24 to allow such a connection. Similarly, a Bur guide cartridge (not shown) may be attached to cartridge engaging portion 20 as described above for paddle cartridge 50. Such a Bur guide cartridge may have a recess (not shown) for receiving upwardly projecting portion 25 to allow such a connection.

Open saw guide 250 may be utilized for an open procedure while a Bur guide (not shown) may be used for a MIS (Minimally Invasive Surgery) procedure. Such an open procedure could involve an incision (e.g., of 4-5 cm) over a proximal metatarsal and medial cuneiform, for example, while an MIS procedure would involve incisions only at the locations necessary for the insertion of particular instruments (e.g., paddle 55). For example, a Bur guide cartridge (not shown) may include a 2.3 mm Shannon Burr usable to bur a joint space. In another example, if an open procedure is done (e.g., without the use of a cut guide) with Curettage or Microfracture then a cut guide cartridge would not be needed and thus not attached to cartridge engaging portion 20.

Figure 15:
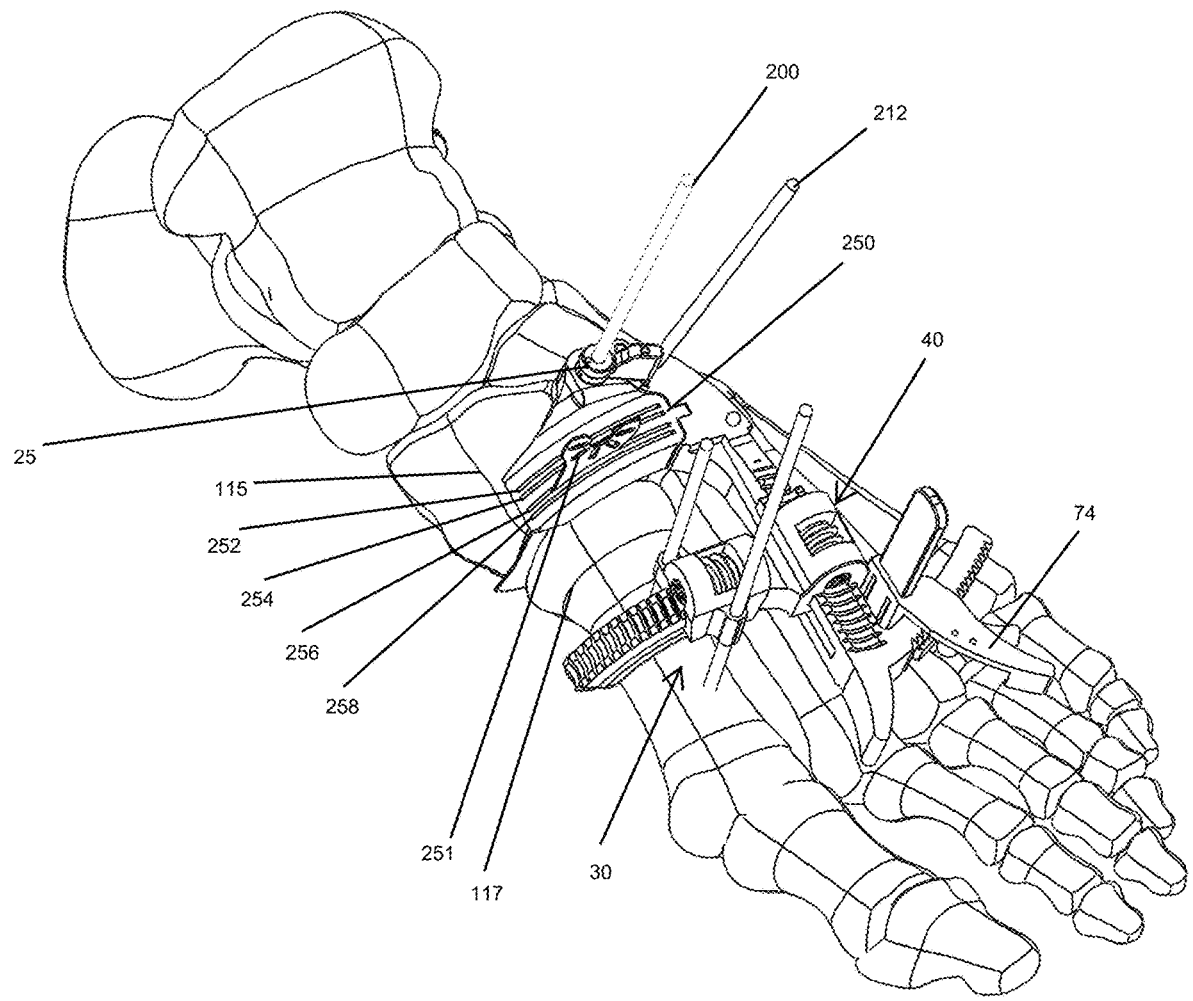
FIG. 15 is a perspective view of the system of FIG. 14 with a saw guide received in a saw slot of the open cut guide.
Figure 16:
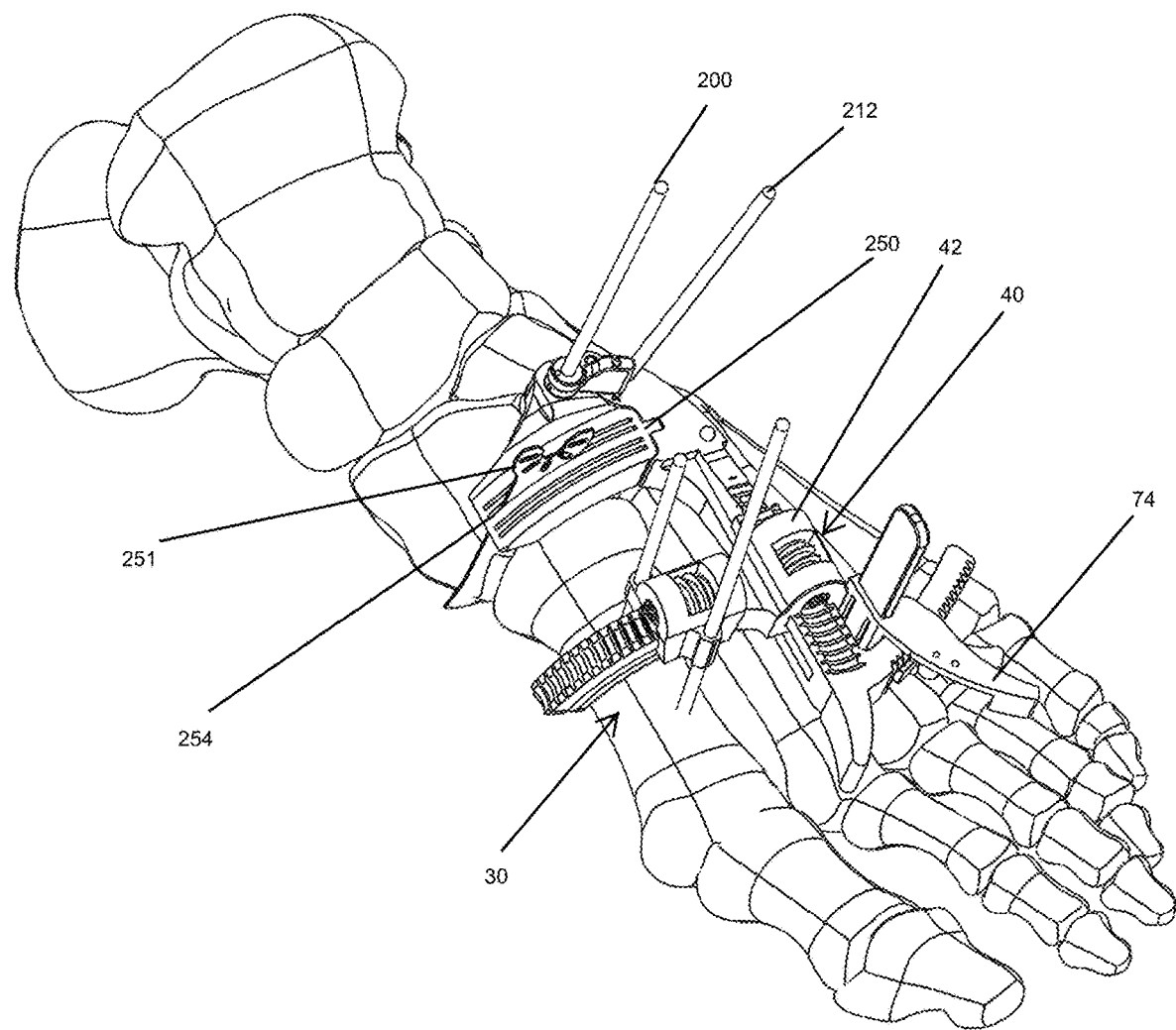
FIG. 16 is a perspective view of the system of FIG. 15 with the saw guide received in a different slot of the open saw guide relative to FIG. 15.
Figure 20:
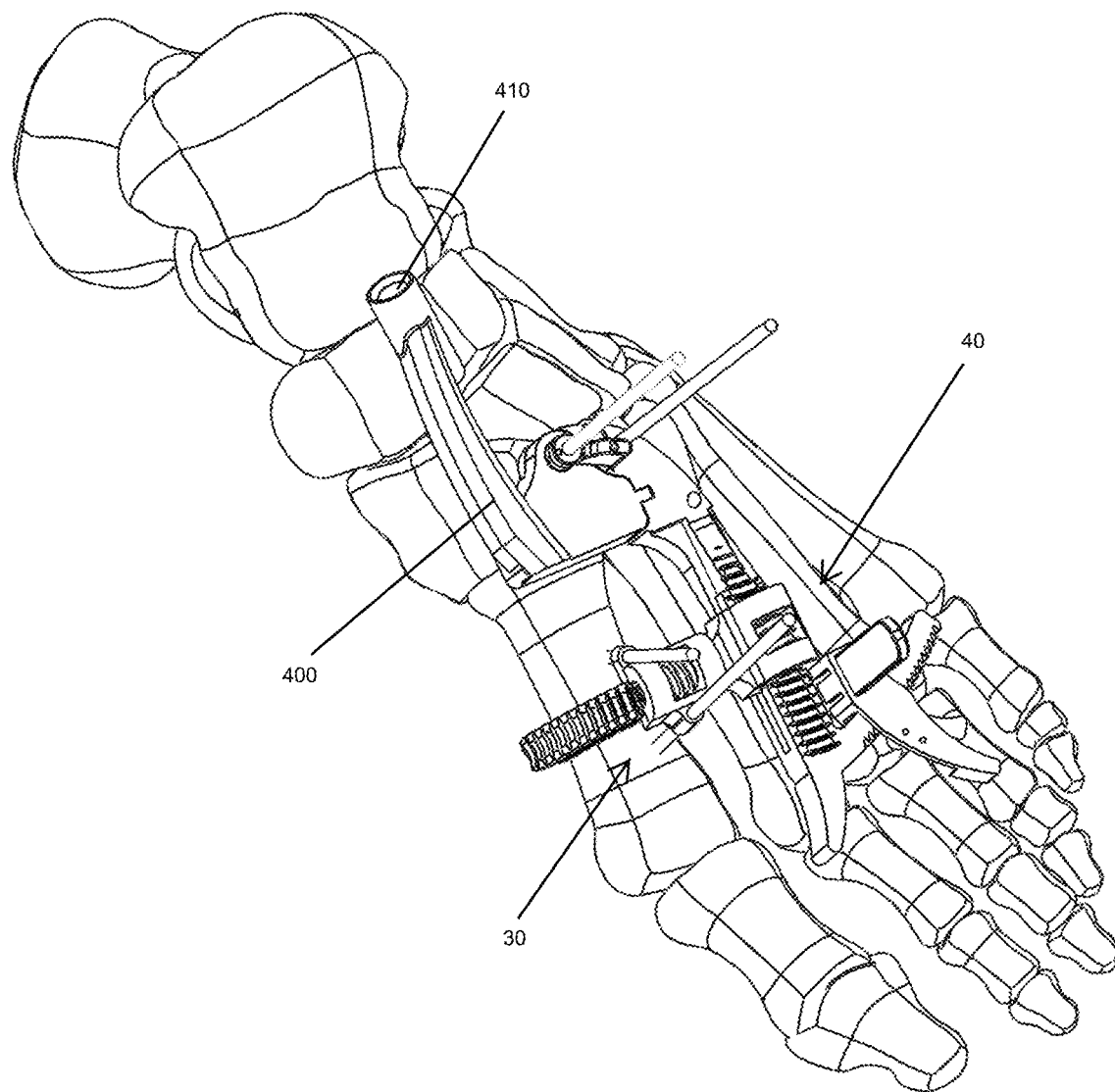
FIG. 20 is a perspective view of the system of FIG. 19 showing a screw guide connected to the cartridge engaging portion of the system of FIG. 1 to provide a guide for screwing to connect the cuneiform and metatarsal.

As depicted in FIG. 15 open saw guide 250 includes a first 1.5 mm cutting slot 252 and a first 3 mm cutting slot 253 to be utilized for cutting a cuneiform (e.g., proximal cuneiform 115) and a second 1.5 mm cutting slot 256 and a second 3 mm cutting slot 258 to be utilized for cutting a Metatarsal (e.g., first metatarsal 117), respectively, for example. FIG. 15 depicts such a cut of metatarsal 117 via slot 256 via slot 256 using a saw 251 and FIG. 20 depicts such a cut of proximal cuneiform 115 via slot 254.

Figure 17:
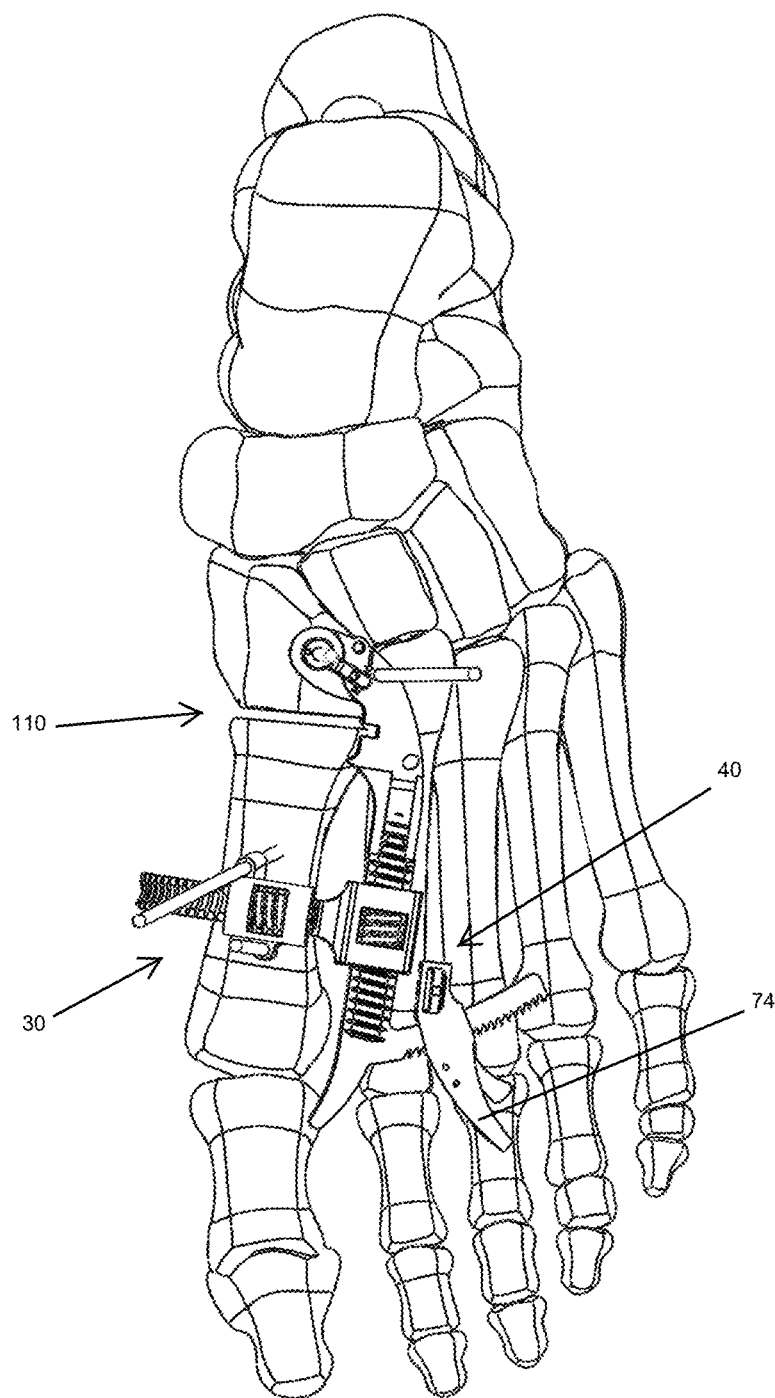
FIG. 17 is a top view of the system of FIG. 16 showing a space between the cuneiform and metatarsal.

As depicted in FIG. 17, any connected cartridge (e.g., paddle cartridge 50, open saw guide 250, a Bur guide cartridge) may be removed to reveal a joint space for easy access (for open cutting) to a joint (e.g., joint space 110) between a cuneiform and metatarsal, for example.

Figure 18:
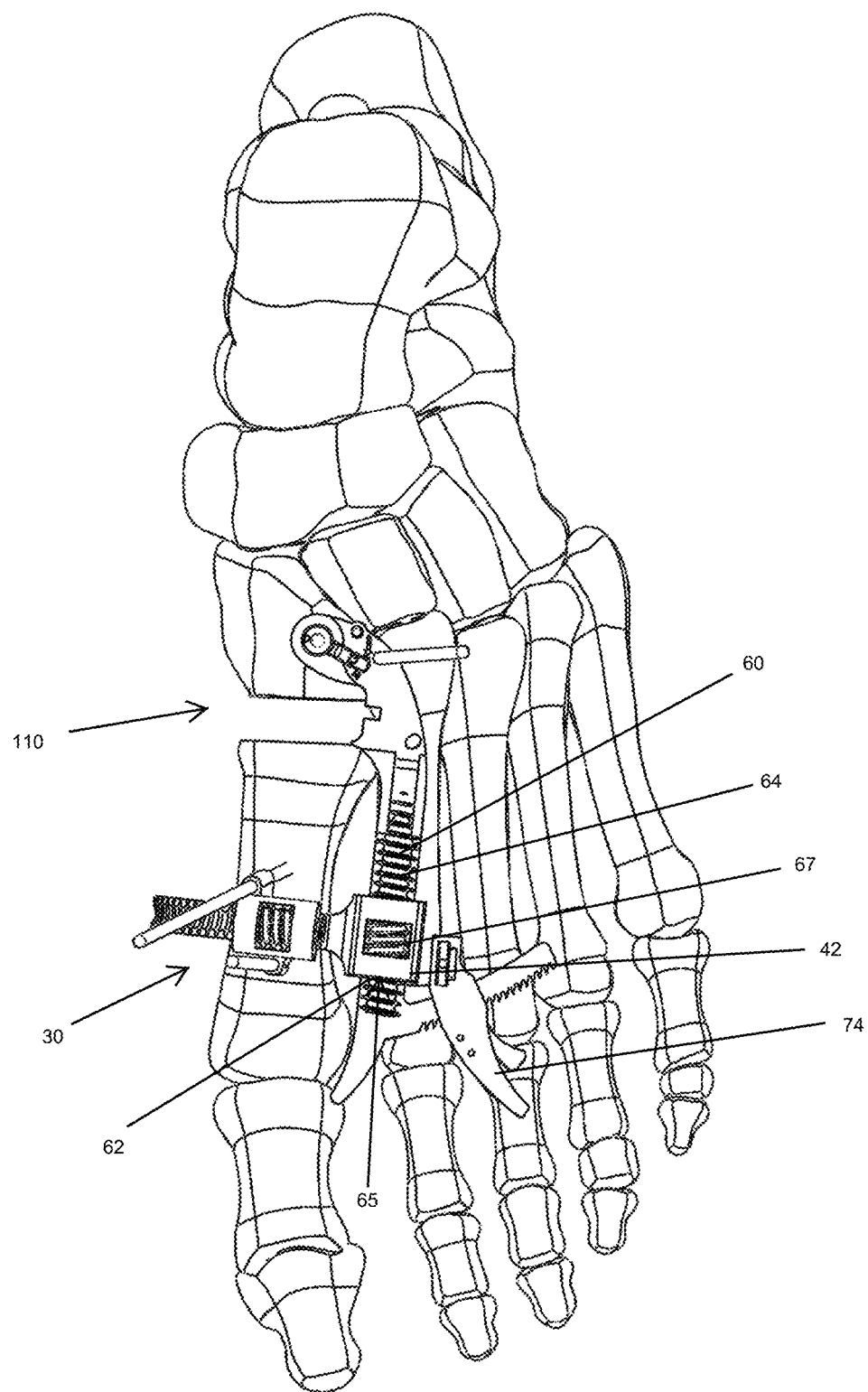
FIG. 18 is a top view of the system of FIG. 17 showing a space between the cuneiform and metatarsal larger after distraction.

As depicted in FIG. 18, a driver (e.g., a torx driver) may be inserted into a recess 65 of end portion 62 of mobile portion 42 of distraction mechanism 40 to rotate a worm screw 67 received in an interior cavity 47 of mobile portion 42. Worm screw 67 may engage an interior threaded surface (not shown) of mobile portion 42 bounding cavity 47 and a top threaded surface 64 of arm 60. A rotation of the driver and worm screw 67 counter clockwise may cause movement of mobile portion 42 along arm 60 due to the engagement of worm gear 67 with threaded surface 64 and the interior threaded surface of mobile portion 42 to cause a movement of trolley 30 connected to first metatarsal 117 to distract a Tarsometatarsal joint (e.g., joint 110) for final preparation, as depicted.

Figure 19:
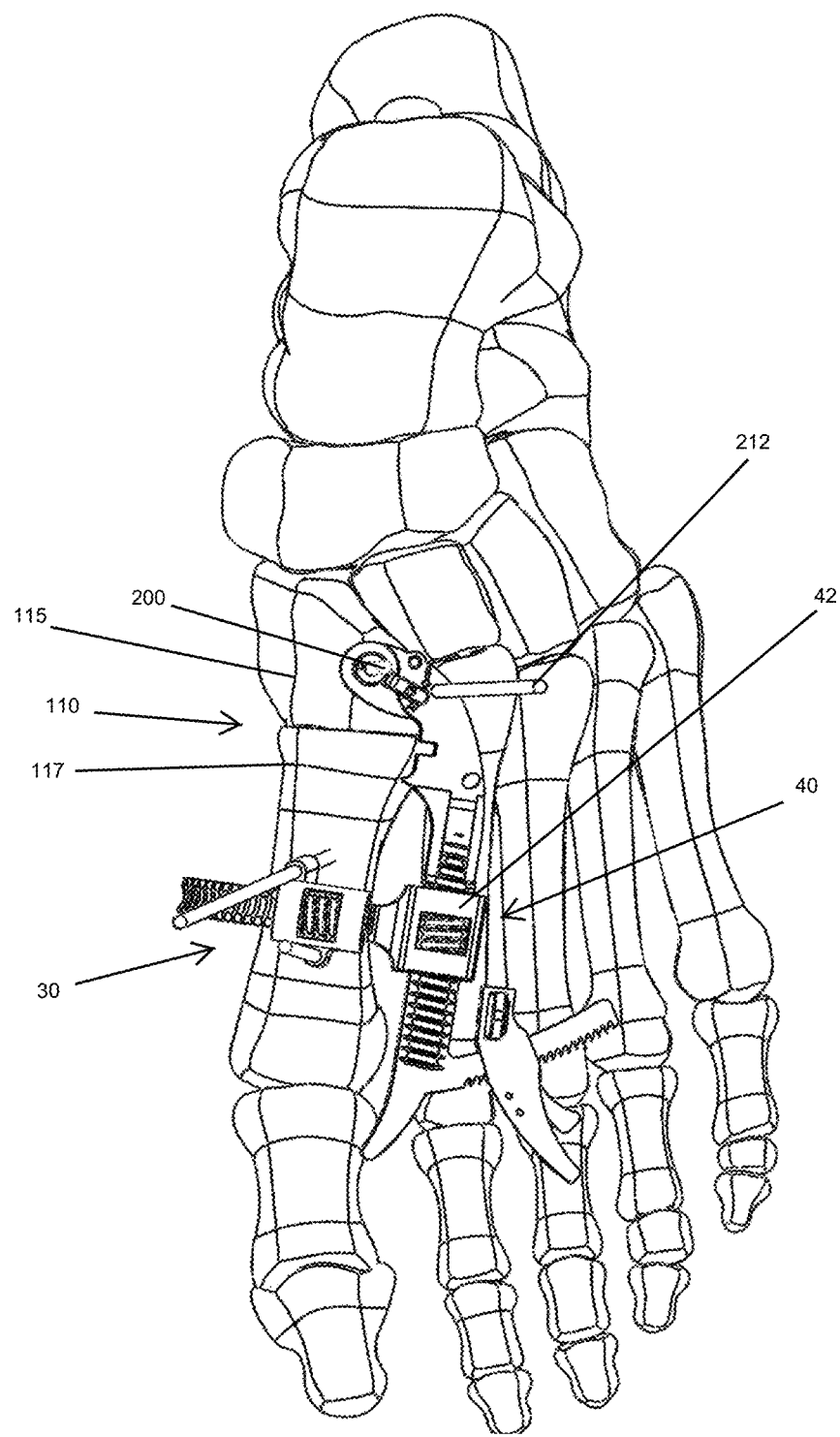
FIG. 19 is a top view of the system of FIG. 18 showing the cuneiform and metatarsal after compression.

After the bones (e.g., proximal cuneiform 115, first metatarsal 117) bounding a joint (e.g., joint 110) have been cut as described above (e.g., using open saw guide 250 and saw 251) or otherwise prepared, the driver may be engaged with worm gear 67 as described above and rotated clockwise, for example, to move mobile portion 42 along arm 60 to move trolley 30 to thereby move a metatarsal (e.g., first metatarsal 117) toward a cuneiform (e.g., proximal cuneiform 115) to compress or close the joint as depicted in FIG. 19. A plate, such as a medial Lapidus plate 300 (FIG. 24), may be attached to the bones (e.g., proximal cuneiform 115, first metatarsal 117) on each side of the joint (e.g., joint 110) to connect the bones.

Figure 21:
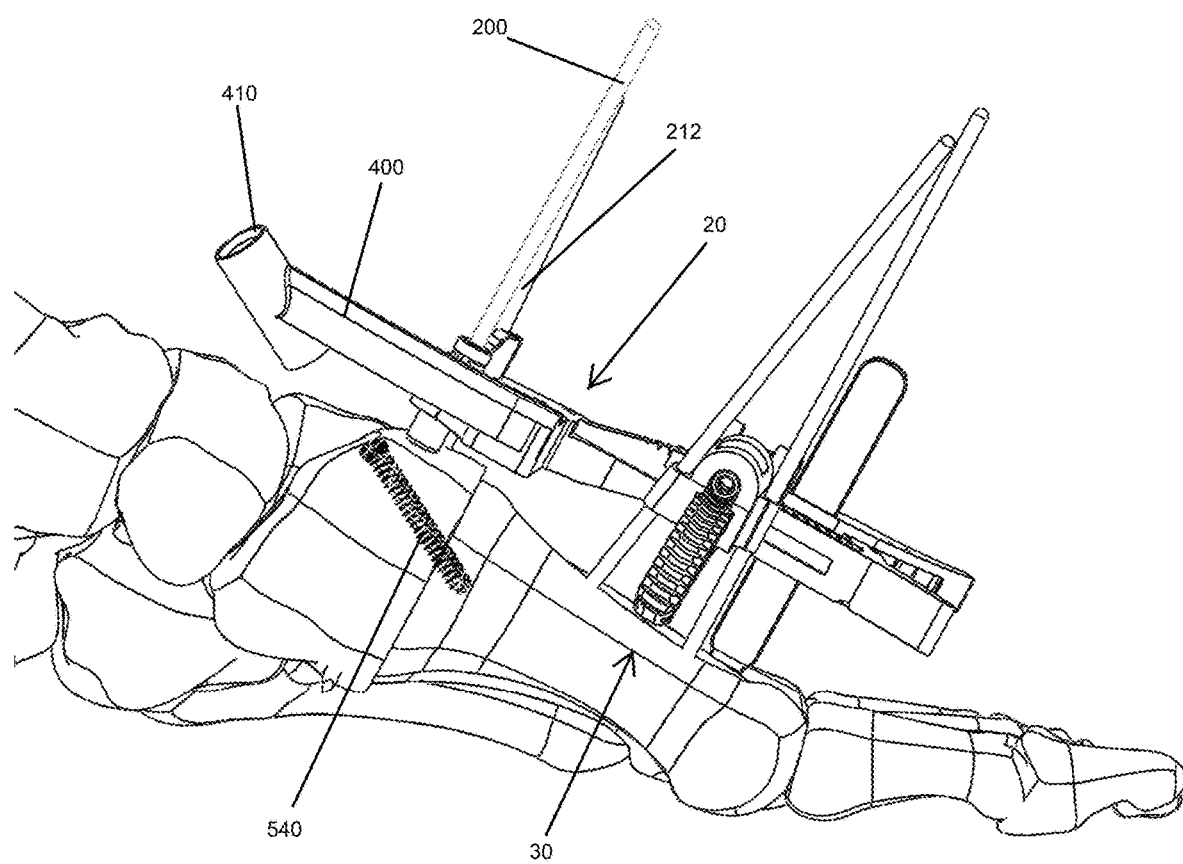
FIG. 21 is a side view of the system of FIG. 20 showing a screw inserted into the bones.
Figure 22:
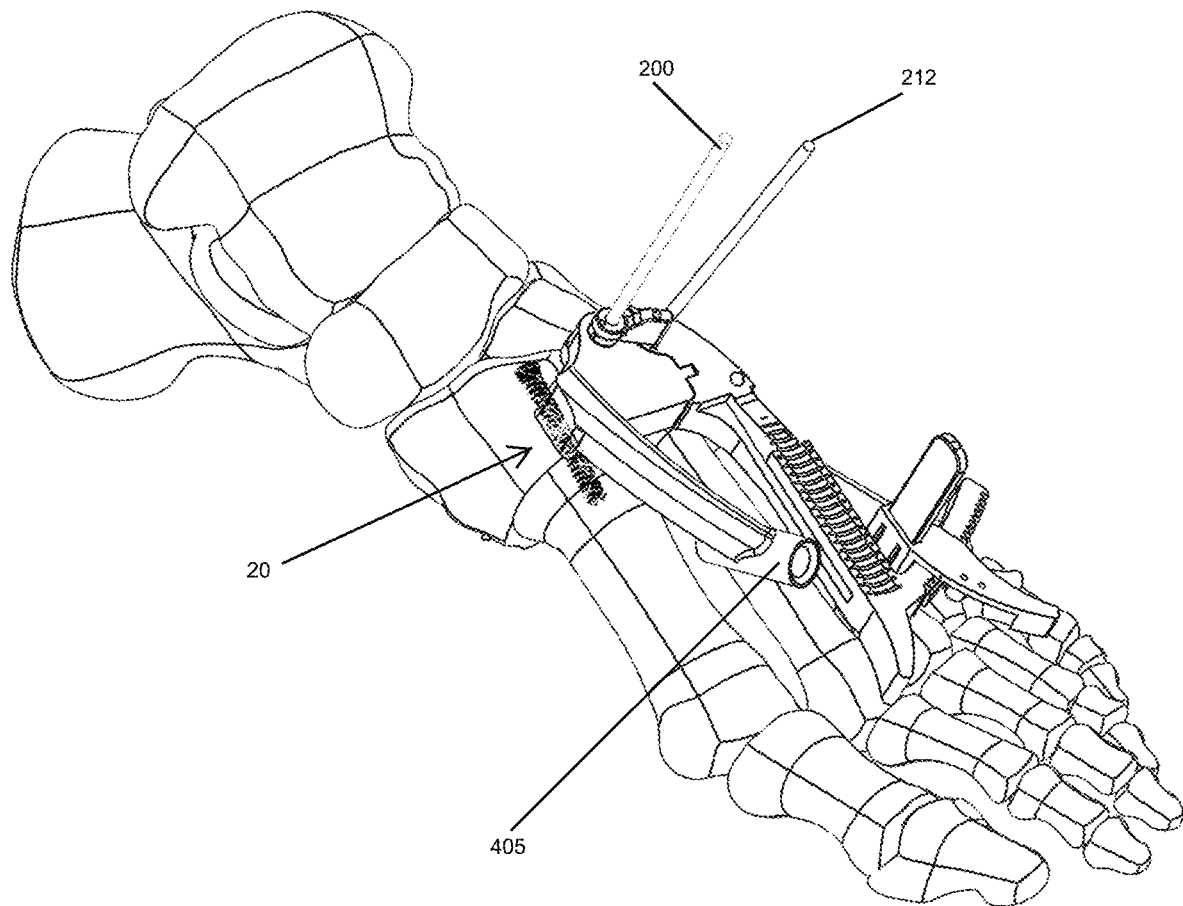
FIG. 22 is a perspective view of the system of FIG. 21 showing a second screw guide connected to the cartridge engaging portion of the system of FIG. 1 to provide a guide for screwing to connect the cuneiform and metatarsal.
Figure 23:
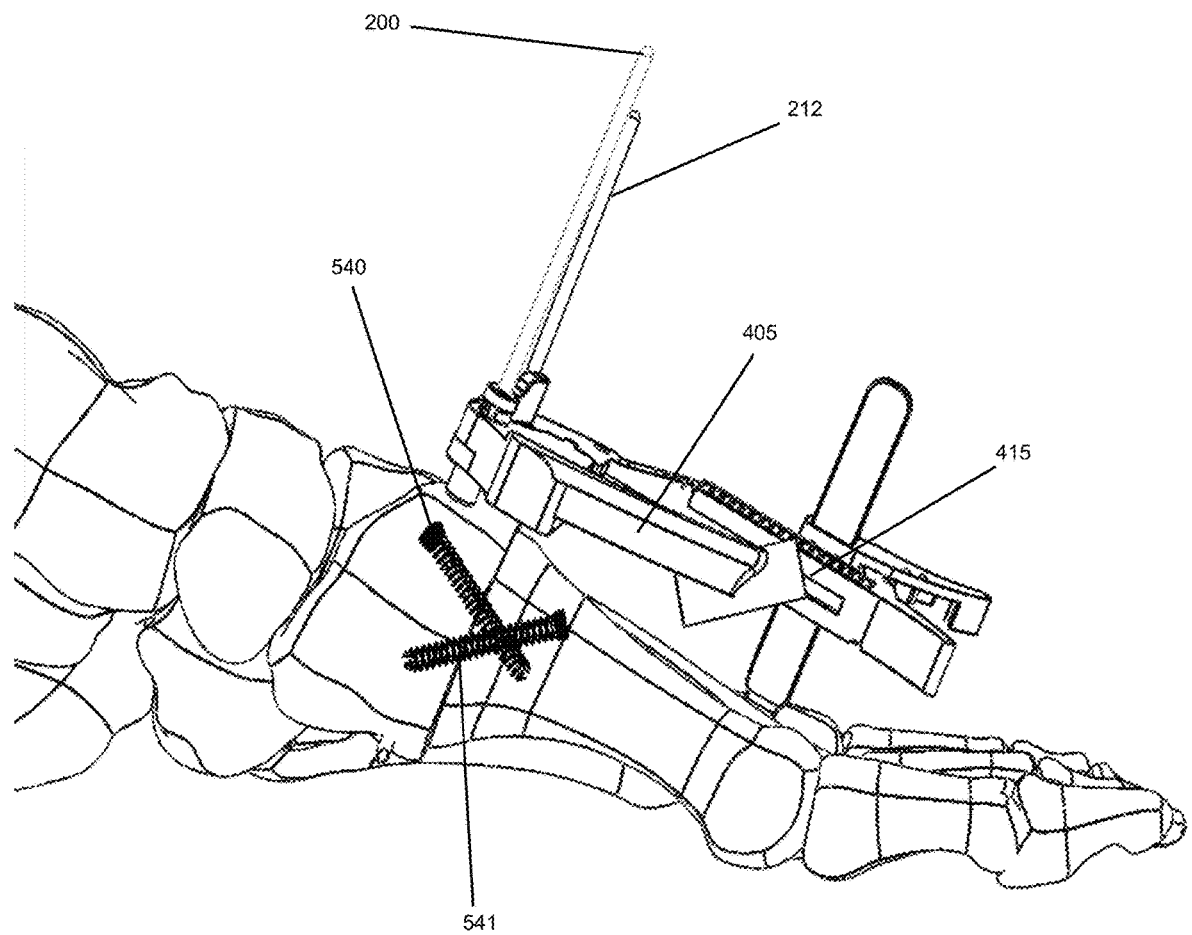
FIG. 23 is a side view of the system of FIG. 22 showing a second screw inserted into the bones.
Figure 24:
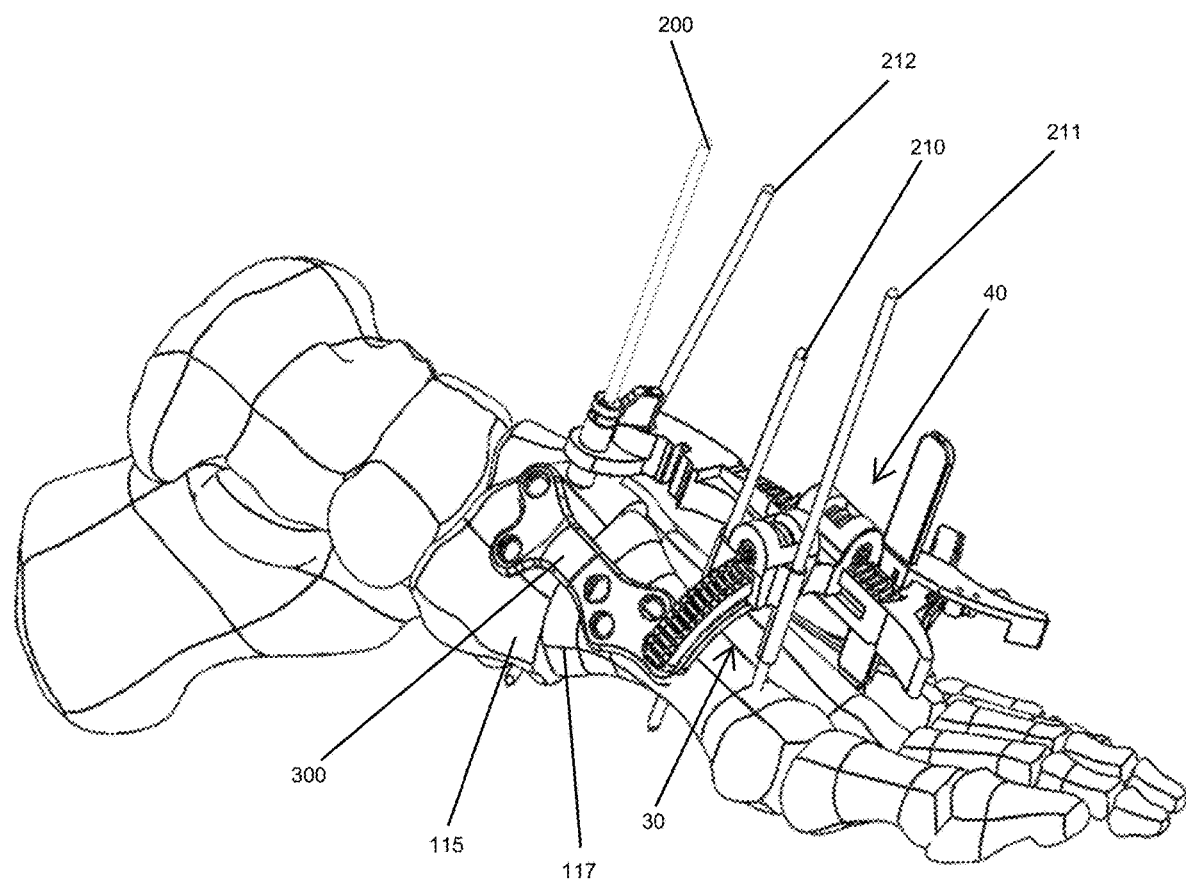
FIG. 24 is a perspective view of the joint between the metatarsal and cuneiform of FIG. 19 with a plate connected thereto.

As depicted in FIG. 20, a screw guide 400 may be connected to cartridge engaging portion 20 as described above relative to paddle cartridge 50. Screw guide 400 may include a first screw alignment slot 410 (e.g., aligned, shaped and dimensioned) to direct a screw 450 therethrough into a desired location to connect two bones (e.g., proximal cuneiform 115, first metatarsal 117) together while avoiding a K-wire (e.g., 200) already present in the bone (e.g., proximal cuneiform 115) as depicted in FIGS. 20-21. A second screw guide 405 may be connected to cartridge engaging portion 20 as described above relative to paddle cartridge 50 as depicted in FIG. 22. Second screw guide 405 may include a second screw alignment slot 415 (e.g., aligned, shaped and dimensioned) to direct a screw 451 therethrough into a desired location to connect two bones (e.g., proximal cuneiform 115, first metatarsal 117) together while avoiding a K-wire (e.g., 200) already present in the bone (e.g., proximal cuneiform 115) as depicted in FIG. 23.

In an undepicted example, K-wires can be placed across a joint (e.g., joint 110) free handed to keep a first metatarsal (e.g., first metatarsal 117) in place while removing system 10 and an interosseous system may be inserted such as that described in U.S. patent application Ser. No. 16/293,382 incorporated herein by reference.

As described above, cartridge engaging portion 20 may connect to other tools or functional elements, such as paddle cartridge 50, open saw guide 250, Bur guide cartridge 270, and screw guide 400 via disc 27, and such elements may also be connected to cartridge engaging portion 20 via other connecting mechanisms in accordance with the described invention in unillustrated examples. Also, other functional elements not described herein desired by a surgeon may be attached to cartridge engaging portion 20 via handle 24 and upwardly projecting portion 25 or other connecting mechanisms.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:
1. A bone displacement system comprising:
an anchoring portion having an aperture for receiving a wire to connect the anchoring portion to a proximal bone;
a tool engaging portion connected to said anchoring portion and configured to connect a tool thereto;
a compression-distraction mechanism connected to said anchoring portion;
a lateral body connected to said compression-distraction mechanism, said lateral body having a downwardly depending portion for contacting a lateral bone; and
a distal body connected to said compression-distraction mechanism, said distal body having an aperture for receiving a wire to connect the distal body to a distal bone, and said compression-distraction mechanism configured to move said anchoring portion relative to said distal body, said distal body comprising a trolley having a mobile portion movably connected to a rail to allow said mobile portion to move laterally relative to a longitudinal axis of said compression-distraction mechanism;
said trolley comprising a screw engaging the rail and the mobile portion to allow movement of the mobile portion and the distal bone relative to the lateral bone when a user drives said screw, the distal body connected to the distal bone and the anchoring portion connected to the proximal bone.

2. The system of claim 1 wherein said tool comprises a paddle, the paddle releasably connected to the tool engaging portion and receivable between the proximal bone and the distal bone for locating the anchoring portion relative to the proximal bone and said distal body relative to the distal bone.

3. The system of claim 1 wherein said tool comprises a cut guide releasably connected to the tool engaging portion and having a first cut slot and a second cut slot for cutting the proximal bone and/or the distal bone.

4. The system of claim 3 wherein the first cut slot and the second cut slot have longitudinal axes substantially parallel to each other.

5. The system of claim 1 wherein said compression-distraction mechanism is connectable to the proximal bone by the anchoring portion and the distal bone by the distal body, said compression-distraction mechanism configured to move the proximal bone relative to the distal bone.

6. The system of claim 5 wherein said compression-distraction mechanism comprises a rack and the screw is engageable by a user to cause movement of the mobile portion relative to the rack to cause a compression or a distraction of the proximal bone relative to the distal bone when the proximal bone is connected to the anchoring portion and the distal bone is connected to the distal body.

7. The system of claim 1 wherein the distal body comprises a third aperture to receive a third wire to connect the distal body to the distal bone.

8. The bone cut guide of claim 1 wherein the rail has a rail longitudinal axis, the mobile portion engaged with a rack and the rack having a rack longitudinal axis, said rail longitudinal axis and said rack longitudinal axis being about perpendicular to each other.

9. The system of claim 1 wherein the lateral body is connected to said compression-distraction mechanism by an arm.

10. The system of claim 1 wherein the lateral body is connected to said compression-distraction mechanism by a holding member that inhibits movement of the lateral body relative to the compression-distraction mechanism.

11. A method for use in bone displacement, comprising:
inserting a first wire through an anchoring portion of a bone displacement mechanism into a first bone;
releasably connecting an alignment paddle to the bone displacement mechanism;
inserting the paddle between the first bone and a second bone;
inserting a second wire through a distal body of the bone displacement mechanism distal to the anchoring portion into the second bone distal to the first bone; and
moving the distal body and the second bone toward a lateral body of the bone displacement mechanism located laterally relative to the distal body and the anchoring portion to adjust an alignment of axes of the first bone and the second bone relative to each other;
wherein the distal body is connected to the anchoring portion and the literal portion by an intermediate body, the intermediate body connected to the lateral body by a ratchet connector and the moving the distal body and the second bone toward the lateral body comprises ratcheting the intermediate body toward the lateral body on the ratchet connector.

12. The method of claim 11 wherein the distal body is connected by the second wire through an aperture of a mobile portion of the distal body to the second bone, and further comprising moving the mobile portion on a rail of the distal body toward the lateral body to rotate the second bone about an axis of the second bone.

13. The method of claim 12 wherein the moving the mobile portion comprises providing a force by a second paddle of the lateral body depending downwardly against a third bone.

14. The method of claim 12 further comprising releasably connecting a bone cut guide to the bone displacement mechanism and cutting the first bone through a slot of the bone cut guide and cutting the second bone through a second slot of the bone cut guide.

15. The method of claim 14 further comprising distracting the second bone relative to the first bone by moving an arm mobile portion of the intermediate body on a rack of the intermediate body, the arm mobile portion connected to the rail such that the moving the arm mobile portion moves the distal body and the second bone.

16. The method of claim 15 further comprising compressing the second bone toward the first bone by moving the arm mobile portion of the intermediate body on the rack proximally toward the anchoring portion.

17. The method of claim 16 further comprising releasably connecting a screw guide to the bone displacement mechanism and connecting the first bone to the second bone by a screw through the screw guide.

18. The method of claim 17 further comprising releasably connecting a second paddle to the lateral body depending downwardly and contacting a third bone.

19. The method of claim 18 wherein the moving the distal body and the second bone toward the lateral body comprises providing a force by the second paddle against the third bone to allow the ratcheting of the intermediate body toward the lateral body.

20. The method of claim 15 wherein the rail and the rack have longitudinal axes aligned about perpendicular to each other.

21. A bone displacement system comprising:
an anchoring portion having an aperture for receiving a wire to connect the anchoring portion to a proximal bone;
a tool engaging portion connected to said anchoring portion and configured to connect a tool thereto;
a compression-distraction mechanism connected to said anchoring portion;
a lateral body connected to said compression-distraction mechanism, said lateral body having a downwardly depending portion for contacting a lateral bone; and
a distal body connected to said compression-distraction mechanism, said distal body having an aperture for receiving a wire to connect the distal body to a distal bone, and said compression-distraction mechanism configured to move said anchoring portion relative to said distal body; and
wherein said tool comprises a paddle, the paddle releasably connected to the tool engaging portion and receivable between the proximal bone and the distal bone for locating the anchoring portion relative to the proximal bone and said distal body relative to the distal bone.

22. A bone displacement system comprising:
an anchoring portion having an aperture for receiving a wire to connect the anchoring portion to a proximal bone;
a tool engaging portion connected to said anchoring portion and configured to connect a tool thereto;
a compression-distraction mechanism connected to said anchoring portion;
a lateral body connected to said compression-distraction mechanism, said lateral body having a downwardly depending portion for contacting a lateral bone; and
a distal body connected to said compression-distraction mechanism, said distal body having an aperture for receiving a wire to connect the distal body to a distal bone, and said compression-distraction mechanism configured to move said anchoring portion relative to said distal body; and
wherein said tool comprises a cut guide releasably connected to the tool engaging portion and having a first cut slot and a second cut slot for cutting the proximal bone and/or the distal bone.

23. A bone displacement system comprising:
an anchoring portion having an aperture for receiving a wire to connect the anchoring portion to a proximal bone;
a tool engaging portion connected to said anchoring portion and configured to connect a tool thereto;
a compression-distraction mechanism connected to said anchoring portion;
a lateral body connected to said compression-distraction mechanism, said lateral body having a downwardly depending portion for contacting a lateral bone; and
a distal body connected to said compression-distraction mechanism, said distal body having an aperture for receiving a wire to connect the distal body to a distal bone, and said compression-distraction mechanism configured to move said anchoring portion relative to said distal body; and
said compression-distraction mechanism connectable to the proximal bone by the anchoring portion and the distal bone by the distal body, said compression-distraction mechanism configured to move the proximal bone relative to the distal bone; and
said compression distraction mechanism comprising a rack mobile portion, a rack and a screw engageable by a user to cause movement of the rack mobile portion relative to the rack to cause a compression or a distraction of the proximal bone relative to the distal bone when the proximal bone is connected to the anchoring portion and the distal bone is connected to the distal body.

24. A bone displacement system comprising:

an anchoring portion having an aperture for receiving a wire to connect the anchoring portion to a proximal bone;

a tool engaging portion connected to said anchoring portion and configured to connect a tool thereto;

a compression-distraction mechanism connected to said anchoring portion;

a lateral body connected to said compression-distraction mechanism, said lateral body having a downwardly depending portion for contacting a lateral bone; and a distal body connected to said compression-distraction mechanism, said distal body having an aperture for receiving a wire to connect the distal body to a distal bone, and said compression-distraction mechanism configured to move said anchoring portion relative to said distal body; and said distal body comprising a trolley mobile portion moveably engaged with a rail and the rail has a rail longitudinal axis, the compression distraction mechanism having an arm mobile portion engaged with a rack and the rack having a rack longitudinal axis, said rail longitudinal axis and said rack longitudinal axis being about perpendicular to each other.

\* \* \* \* \*

UNITED STATES PATENT AND TRADEMARK OFFICE
CERTIFICATE OF CORRECTION

| | | |
|---|---|---|
| PATENT NO. | : 11,849,933 B2 | Page 1 of 1 |
| APPLICATION NO. | : 17/238920 | |
| DATED | : December 26, 2023 | |
| INVENTOR(S) | : Denham et al. | |

It is certified that error appears in the above-identified patent and that said Letters Patent is hereby corrected as shown below:

In the Claims

Column 8, Line 58: Claim 8, Delete "axis, said rail" and insert -- axis, the compression distraction mechanism having an arm mobile portion engaged with a rack and the rack having a rack longitudinal axis, said rail --

Signed and Sealed this
Twenty-third Day of July, 2024

Katherine Kelly Vidal
*Director of the United States Patent and Trademark Office*